(12) United States Patent
Lybarger et al.

(10) Patent No.: US 11,786,739 B2
(45) Date of Patent: Oct. 17, 2023

(54) VENTRICULAR SENSING CONTROL IN A CARDIAC PACING SYSTEM

(71) Applicant: Medtronic, Inc., Minneapolis, MN (US)

(72) Inventors: Maureen E. Lybarger, New Brighton, MN (US); Jian Cao, Shoreview, MN (US); Wade M. Demmer, Coon Rapics, MN (US); Michael W. Heinks, New Brighton, MN (US); Jean E. Hudson, Blaine, MN (US); Michael Kemmerer, Victoria, MN (US); James J. St. Martin, Blaine, MN (US); Todd J. Sheldon, North Oaks, MN (US)

(73) Assignee: Medtronic Inc., Minneapolis, MN (US)

(*) Notice: Subject to any disclaimer, the term of this patent is extended or adjusted under 35 U.S.C. 154(b) by 435 days.

(21) Appl. No.: 16/995,965

(22) Filed: Aug. 18, 2020

(65) Prior Publication Data

US 2021/0052895 A1 Feb. 25, 2021

Related U.S. Application Data

(60) Provisional application No. 62/888,570, filed on Aug. 19, 2019.

(51) Int. Cl.
| A61N 1/36 | (2006.01) |
| A61N 1/362 | (2006.01) |
| A61N 1/365 | (2006.01) |
| A61B 5/352 | (2021.01) |

(52) U.S. Cl.
CPC ............ *A61N 1/3624* (2013.01); *A61B 5/352* (2021.01); *A61N 1/365* (2013.01)

(58) Field of Classification Search
CPC .... A61N 1/3624; A61N 1/365; A61N 1/3756; A61N 1/3704; A61N 1/057; A61N 1/368; A61N 1/39622; A61B 5/352
See application file for complete search history.

(56) References Cited

U.S. PATENT DOCUMENTS

| 4,967,746 A | 11/1990 | Vandegriff |
| 5,339,820 A * | 8/1994 | Henry ................ A61N 1/3704 600/508 |
| 5,755,739 A | 5/1998 | Sun |
| 7,383,091 B1 | 6/2008 | Chitre |
| 7,567,835 B2 | 7/2009 | Gunderson |
| 7,813,798 B2 | 10/2010 | Bornzin |
| 9,468,766 B2 | 10/2016 | Sheldon et al. |

(Continued)

OTHER PUBLICATIONS (PCT/US2020/046897) PCT Notification of Transmittal of the International Search Report and the Written Opinion of the International Searching Authority, dated Nov. 23, 2020, 11 pages.

(Continued)

*Primary Examiner* — Rex R Holmes

(57) ABSTRACT

A medical device is configured to set a post-atrial time interval in response to an atrial event and generate an event time signal in response to a ventricular electrical signal crossing an R-wave sensing threshold during the post-atrial time interval. The device accumulates oversensing evidence in response to the event time signal and adjusts a ventricular sensing control parameter based on the accumulated oversensing evidence in some examples.

33 Claims, 9 Drawing Sheets

(56) References Cited

U.S. PATENT DOCUMENTS

| | | |
|---|---|---|
| 9,724,519 B2 | 8/2017 | Demmer et al. |
| 2005/0021095 A1* | 1/2005 | Rueter .................. A61N 1/3712 607/9 |
| 2016/0235315 A1 | 8/2016 | Sarkar et al. |
| 2017/0312534 A1 | 11/2017 | Cao et al. |
| 2017/0354827 A1 | 12/2017 | Zhang et al. |
| 2019/0083800 A1 | 3/2019 | Yang et al. |
| 2019/0134404 A1 | 5/2019 | Sheldon et al. |

OTHER PUBLICATIONS

Brown, Mark L., et al. "Sensing and detection in Medtronic implantable cardioverter defibrillators," Herzschrittmachertherapie und Elktrophysiologie; Steinkopff, Darmstadt, DE; vol. 27, No. 3, Sep. 8, 2016, pp. 193-212.

* cited by examiner

VENTRICULAR SENSING CONTROL IN A CARDIAC PACING SYSTEM

REFERENCE TO RELATED APPLICATION

This application claims the benefit of U.S. Patent Application No. 62/888,570, filed provisionally on Aug. 19, 2019 and incorporated herein by reference in its entirety.

TECHNICAL FIELD

This disclosure relates to a medical device and method for controlling sensing of ventricular events based on evidence of oversensing.

BACKGROUND

During normal sinus rhythm (NSR), the heartbeat is regulated by electrical signals produced by the sino-atrial (SA) node located in the right atrial wall. Each atrial depolarization signal produced by the SA node spreads across the atria, causing the depolarization and contraction of the atria, and arrives at the atrioventricular (AV) node. The AV node responds by propagating a ventricular depolarization signal through the bundle of His of the ventricular septum and thereafter to the bundle branches and the Purkinje muscle fibers of the right and left ventricles, sometimes referred to as the "His-Purkinje system."

Patients with a conduction system abnormality, e.g., poor AV node conduction, poor SA node function, or other conduction abnormalities, may receive a pacemaker to restore a more normal heart rhythm and AV synchrony. Ventricular pacing may be performed to maintain the ventricular rate in a patient having atrioventricular conduction abnormalities. A single chamber ventricular pacemaker may be coupled to a transvenous ventricular lead carrying electrodes placed in the right ventricle, e.g., in the right ventricular apex. The pacemaker itself is generally implanted in a subcutaneous pocket with the transvenous ventricular lead tunneled to the subcutaneous pocket. Intracardiac pacemakers have been introduced or proposed for implantation entirely within a patient's heart, eliminating the need for transvenous leads. An intracardiac pacemaker may provide sensing and pacing from within a chamber of the patient's heart, e.g., from within the right ventricle in a patient having AV conduction block.

Dual chamber pacemakers are available which include a transvenous atrial lead carrying electrodes which are placed in the right atrium and a transvenous ventricular lead carrying electrodes that are placed in the right ventricle via the right atrium. A dual chamber pacemaker senses atrial electrical signals and ventricular electrical signals and can provide both atrial pacing and ventricular pacing as needed to promote a normal atrial and ventricular rhythm and promote AV synchrony when SA and/or AV node or other conduction abnormalities are present.

Ventricular pacing via electrodes at or near the right ventricular apex has been found to be associated with increased risk of atrial fibrillation and heart failure. Alternative pacing sites have been investigated or proposed, such as pacing of the His bundle. Cardiac pacing of the His bundle has been proposed to provide ventricular pacing along the heart's natural conduction system. Pacing the ventricles via the His bundle allows recruitment along the heart's natural conduction system, including the Purkinje fibers, and is hypothesized to promote more physiologically normal cardiac activation than other pacing sites, such as the ventricular apex.

SUMMARY

The techniques of this disclosure generally relate to controlling ventricular sensing in a medical device capable of pacing the heart. The medical device is capable of delivering ventricular pacing pulses, which may be delivered to the His bundle or along the His-Purkinje system in some examples. A medical device operating according to the techniques disclosed herein detects evidence of oversensing by a ventricular channel of the medical device and adjusts a ventricular sensing control parameter according to the oversensing evidence. The evidence of oversensing may relate to atrial event oversensing and/or cardiac potential signal oversensing. Among the ventricular sensing control parameters that may be adjusted are a post-atrial ventricular blanking period, a post-atrial safety pace interval, and/or the ventricular sensitivity setting used in controlling an R-wave sensing threshold for sensing ventricular R-waves.

In one example, the disclosure provides a medical device including a sensing circuit configured to sense a ventricular electrical signal, set an R-wave sensing threshold, set a post-atrial time interval in response to receiving an atrial event signal, and generate an event time signal in response to the ventricular electrical signal being equal to or greater than the R-wave sensing threshold during the post-atrial time interval. The medical device further includes a control circuit configured to determine a count of event time signals generated by the sensing circuit and adjust a ventricular sensing control parameter based on the count of event time signals.

In another example, the disclosure provides a method including sensing a ventricular electrical signal, setting an R-wave sensing threshold, receiving an atrial event signal, setting a post-atrial time interval in response to receiving the atrial event signal and generating an event time signal in response to the ventricular electrical signal being equal to or greater than the R-wave sensing threshold during the post-atrial time interval. The method includes determining a count of event time signals and adjusting a ventricular sensing control parameter based on the count of event time signals.

In yet another example, the disclosure provides a non-transitory, computer-readable storage medium storing a set of instructions which, when executed by a control circuit of a medical device cause the medical device to sense a ventricular electrical signal, set an R-wave sensing threshold, receive an atrial event signal, set a post-atrial time interval in response to receiving the atrial event signal, generate an event time signal in response to the ventricular electrical signal being equal to or greater than the R-wave sensing threshold during the post-atrial time interval, determine a count of event time signals and adjust a ventricular sensing control parameter based on the count of event time signals.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
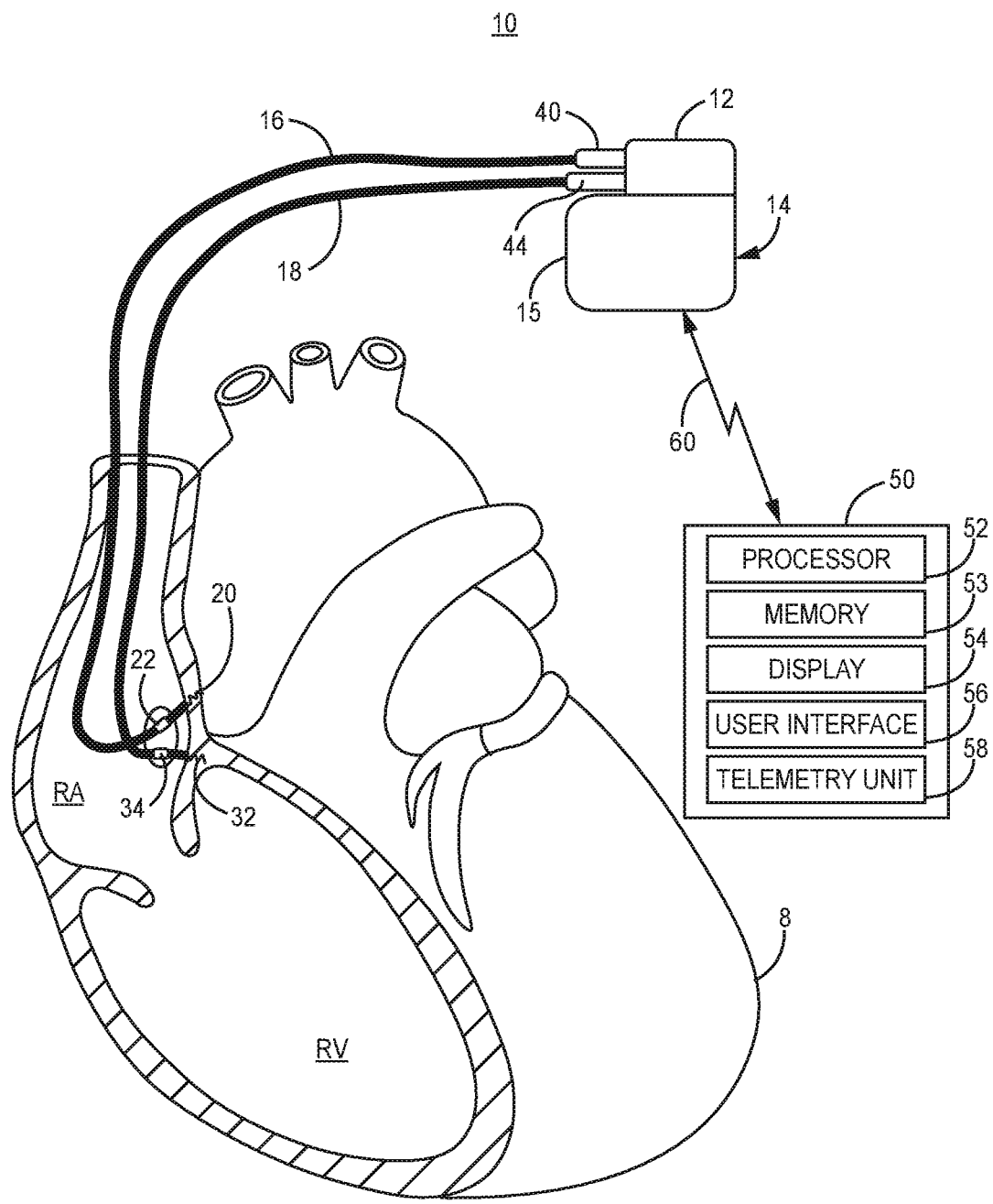
FIG. 1 is a conceptual diagram of an implantable medical device (IMD) system capable of pacing a patient's heart and sensing cardiac electrical signals.

A medical device system capable of generating and delivering ventricular pacing pulses and sensing cardiac electrical signals is described herein. When ventricular electrodes are positioned for sensing ventricular signals and delivering pacing pulses to or in the vicinity of the His bundle, the ventricular electrodes may also be in relatively close proximity to an atrial chamber. As a result, a cardiac electrical signal received by the ventricular sensing electrodes may include P-waves attendant to intrinsic atrial depolarizations, atrial pacing pulse artifacts, and atrial evoked response signals following an atrial pacing pulse. Any of these atrial events present in the ventricular sensing signal may be falsely sensed as an R-wave by the medical device. Falsely sensing an atrial event as an R-wave is referred to herein "atrial event oversensing."

In some cases, a His bundle potential signal or a bundle branch potential signal, referred to herein as "cardiac potential signals," which may precede a QRS waveform, may be present in the ventricular sensing signal, particularly when a sensing electrode is in the vicinity of the His bundle or bundle branches. For instance, a His bundle potential signal, also referred to herein as an "H-wave," may be falsely oversensed as an R-wave when the amplitude of the H-wave crosses an R-wave sensing threshold. Thus the term "oversensing" as used herein may relate to oversensing of atrial events and/or cardiac potential signals produced by the His-Purkinje system that precede ventricular myocardial depolarization. For example, an H-wave may occur between a true atrial event and a true R-wave. An H-wave following an atrial event may or may not be followed by an intrinsically conducted R-wave depending on the presence of a conduction block along the His-Purkinje system. In some cases, therefore, an oversensed H-wave or other cardiac potential signal generated by the His-Purkinje system may result in withholding of a ventricular pacing pulse, which may result in ventricular asystole or a pause in the ventricular rhythm when a conduction block exists.

Techniques are disclosed herein for accumulating oversensing evidence, which may or may not include actual oversensing resulting in sensing a false R-wave and consequently producing a false R-wave sensed event signal. As described below, accumulating oversensing evidence may include determining a count of oversensing events. An oversensing event may be identified based on a ventricular electrical signal crossing an R-wave sensing threshold during a post-atrial time interval. An R-wave sensed event signal may or may not be generated in response to the R-wave sensing threshold crossing that is identified as an oversensing event. The R-wave sensed event signal may or may not be generated depending on whether the sensing threshold crossing occurs during a post-atrial blanking interval. As such, the oversensing event may or may not be an actual oversensed event.

A medical device as disclosed herein controls ventricular sensing control parameters based on the oversensing evidence to avoid or reduce the likelihood of falsely sensing atrial events and/or cardiac potential signals as R-waves. Such oversensing may cause the medical device to withhold a ventricular pacing pulse, which may result in ventricular asystole or a pause in the ventricular rhythm, which may reduce the benefits and effectiveness of a pacing therapy or even cause patient symptoms. By controlling ventricular sensing control parameters based on oversensing evidence using the techniques disclosed herein, the overall medical device performance is improved. The reliability and specificity of ventricular R-wave sensing is improved, and subsequently the effectiveness of a delivered pacing therapy is improved because withholding or delivery of ventricular pacing pulses is based upon the more reliable R-wave sensing.

FIG. 1 is a conceptual diagram of a medical device system 10 capable of pacing a patient's heart 8 and sensing cardiac electrical signals. The system 10 includes an implantable medical device (IMD) 14 coupled to a patient's heart 8 via transvenous medical electrical leads 16 and 18. IMD 14 is shown as a dual chamber device capable of delivering cardiac pacing pulses and sensing cardiac electrical signals in an atrial chamber and in a ventricular chamber. IMD housing 15 encloses internal circuitry corresponding to the various circuits and components described in conjunction with FIG. 4 below, for sensing cardiac signals from heart 8 and controlling electrical stimulation therapy, e.g., pacing therapy, delivered by IMD 14. In particular, circuitry enclosed by housing 15 controls ventricular sensing by adjusting one or more ventricular sensing control parameters in response to detecting evidence of actual or possible oversensing of atrial events and/or cardiac potential signals of the His bundle or bundle branches.

IMD 14 includes a connector block 12 that may be configured to receive the proximal ends of an atrial pacing and sensing lead 16, referred to hereafter as "atrial lead" 16, and a ventricular pacing and sensing lead 18, referred to hereafter as "ventricular lead" 18. Each of leads 16 and 18 are advanced transvenously for positioning electrodes for sensing and stimulation in the atria and the ventricles, respectively. Atrial lead 16 may be positioned such that its distal end is in the vicinity of the right atrium (RA) and the superior vena cava. Atrial lead 16 is equipped with pacing and sensing electrodes, shown as a tip electrode 20 and a ring electrode 22 spaced proximally from tip electrode 20. The electrodes 20 and 22 provide sensing and pacing in the right atrium and are each connected to a respective insulated conductor extending within the elongated body of atrial lead 16. Each insulated conductor is coupled at its proximal end to a connector carried by proximal lead connector 40, and thereby electrically coupled to internal IMD circuitry via connector block 12.

Ventricular lead 18 may be advanced within the right atrium to position electrodes 32 and 34 for pacing and sensing in the vicinity of the His bundle from a right atrial approach, as shown. Ventricular lead tip electrode 32 may be a helical electrode that may be advanced into the inferior end of the interatrial septum, beneath the AV node and near the tricuspid valve annulus to position tip electrode 32 in or proximate to the His bundle. A ring electrode 34 spaced proximally from tip electrode 32 may be used as the return electrode with the cathode tip electrode 32 for pacing the right and left ventricles via the His-Purkinje system. While lead 18 is referred to herein as a ventricular pacing and sensing lead for delivering pacing pulses for pacing the ventricles, ventricular lead 18 may be referred to as a His bundle pacing and sensing lead when positioned for delivering pacing pulses to the ventricles via the His-Purkinje system. It is to be understood that the location of lead 18 and electrodes 32 and 34 shown in FIG. 1 are illustrative in nature and lead 18 and electrodes 32 and 34 may be positioned for delivering pacing pulses to the His bundle, right and/or left bundle branches, Purkinje fibers, or anywhere along the heart's native conduction system to promote depolarization of the right and left ventricles via the heart's native conduction system. In other examples, ventricular lead 18 and electrodes 32 and 34 may be positioned to deliver ventricular pacing pulses to the ventricular myocardium, e.g., along the ventricular septum or a ventricular free wall. As such, electrodes 32 and 34 are not limited to pacing and sensing at or in the vicinity of the His bundle as shown but may be used for delivering ventricular pacing and sensing ventricular R-waves at other locations along the His-Purkinje system or along the ventricular myocardium.

The electrodes 32 and 34 are coupled to respective insulated conductors extending within the elongated body of ventricular lead 18, which provide electrical connection to the proximal lead connector 44 coupled to connector block 12, and thereby electrical connection to IMD circuitry enclosed by housing 15 is achieved. As described below, cardiac electrical signal sensing circuitry included in IMD 14 receives a cardiac electrical signal from electrodes 32 and/or 34 of ventricular lead 18 for sensing ventricular R-waves. Electrodes 32 and 34 may be selected in a bipolar ventricular sensing electrode vector or one electrode carried by ventricular lead 18, e.g., tip electrode 32 or ring electrode 34, may be used in combination with housing 15 for receiving a unipolar, ventricular signal for sensing R-waves by cardiac electrical signal sensing circuitry. While atrial lead 16 and ventricular lead 18 are each shown carrying two electrodes, it is recognized that each lead may carry one or more electrodes for providing one or more selectable pacing and/or sensing electrode vectors, which may include bipolar combinations of electrodes carried by the respective lead or unipolar combinations of an electrode carried by the respective lead and the IMD housing 15.

IMD 14 may be configured as a dual-chamber pacemaker capable of sensing and pacing in the RA and sensing ventricular R-waves and delivering atrial synchronized ventricular pacing pulses in atrial-tracking ventricular pacing modes. In other examples, IMD 14 may be coupled to a single lead advanced into the RA for sensing both atrial and ventricular signals and delivering at least ventricular pacing pulses. IMD 14 may be a single chamber pacing device coupled only to ventricular lead 18 with dual chamber sensing of both atrial and ventricular electrical signals and delivering pacing pulses to the ventricles for at least maintaining a minimum ventricular rate and/or delivering atrial synchronized ventricular pacing. It is to be understood that although IMD 14 is illustrated in FIG. 1 as pacemaker capable of delivering atrial and ventricular pacing, IMD 14 may be configured as an implantable cardioverter defibrillator capable of delivering both low voltage cardiac pacing therapies and high voltage cardioversion and defibrillation (CV/DF) shocks. In this case, IMD 14 may be coupleable to at least one lead carrying at least one high voltage CV/DF electrode such as an elongated coil electrode.

An external device 50 is shown in telemetric communication with IMD 14 by a communication link 60. External device 50 may include a processor 52, memory 53, display unit 54, user interface 56 and telemetry unit 58. Processor 52 controls external device operations and processes data and signals received from IMD 14. Display unit 54, which may include a graphical user interface, displays data and other information to a user for reviewing IMD operation and programmed parameters as well as cardiac electrical signals retrieved from IMD 14. Data obtained from IMD 14 via communication link 60 may be displayed on display 54. For example, a clinician may view cardiac electrical signals and marker channel data received from IMD 14 and/or data derived therefrom. For example, processor 52 may generate a report of oversensing evidence accumulated by IMD 14 and any associated ventricular sensing control parameter adjustments that are made based on the oversensing evidence for display to a user on display 54.

User interface 56 may include a mouse, touch screen, key pad or the like to enable a user to interact with external device 50 to initiate a telemetry session with IMD 14 for retrieving data from and/or transmitting data to IMD 14, including programmable parameters for detecting oversensing evidence and controlling ventricular sensing as described herein. Telemetry unit 58 includes a transceiver and antenna configured for bidirectional communication with a telemetry circuit included in IMD 14 and is configured to operate in conjunction with processor 52 for sending and receiving data relating to IMD functions via communication link 60, which may include data relating to oversensing detection or related data and automatic adjustment of ventricular sensing control parameters.

Communication link 60 may be established between IMD 14 and external device 50 using a wireless radio frequency (RF) link such as BLUETOOTH®, Wi-Fi, or Medical Implant Communication Service (MICS) or other RF or communication frequency bandwidth or communication protocols. Data stored or acquired by IMD 14, including physiological signals or associated data derived therefrom, results of device diagnostics, and histories of detected rhythm episodes and delivered therapies, may be retrieved from IMD 14 by external device 50 following an interrogation command.

External device 50 may be embodied as a programmer used in a hospital, clinic or physician's office to retrieve data from IMD 14 and to program operating parameters and algorithms in IMD 14 for controlling IMD functions. External device 50 may alternatively be embodied as a home monitor or handheld device. External device 50 may be used to program cardiac signal sensing parameters, cardiac rhythm detection parameters and therapy control parameters used by IMD 14. Thresholds or other parameters used for ventricular sensing and oversensing detection according to techniques disclosed herein may be programmed into IMD 14 using external device 50.

Figure 2:
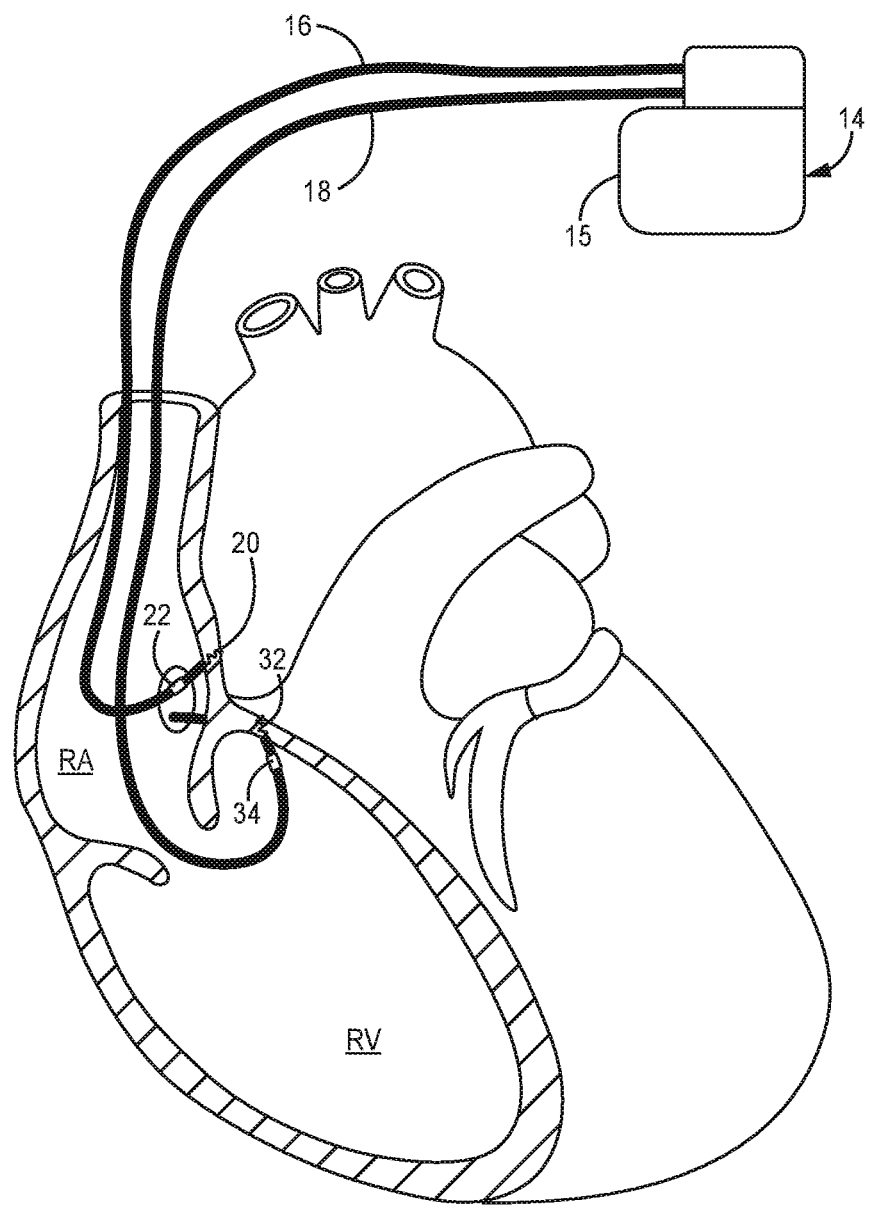
FIG. 2 is a conceptual diagram of the IMD of FIG. 1 coupled to ventricular lead advanced to an alternative ventricular sensing and pacing location.

FIG. 2 is a conceptual diagram of IMD 14 coupled to ventricular lead 18 advanced to an alternative ventricular sensing and pacing location. IMD 14 may be a dual chamber cardiac pacing device coupled to ventricular lead 18 and atrial lead 16. In this example, the distal portion of ventricular lead 18 is advanced within the RV for sensing ventricular electrical signals and delivering ventricular pacing pulses to or in the vicinity of the His bundle or His-Purkinje system from a right ventricular approach.

Tip electrode 32 may be implanted in or along the ventricular septal wall, e.g., high along the ventricular septal wall near the His bundle. Tip electrode 32 may be paired with the return anode ring electrode 34 for delivering ventricular pacing pulses to capture the native ventricular conduction system and/or ventricular myocardium and for sensing a ventricular electrical signal that includes intrinsic R-waves and ventricular evoked response signals. The tip electrode 32 or the ring electrode 34 may be paired with IMD housing 15 for unipolar sensing of ventricular signals in some examples.

When electrodes 32 and 34 are in close proximity to the right atrium, e.g., in either the right atrial approach shown in FIG. 1 or the right ventricular approach shown in FIG. 2, the ventricular sensing circuitry of IMD 14 may falsely sense atrial events as R-waves. When electrodes 32 and 34 are in the vicinity of the His bundle, the His bundle potential signal or H-wave may be falsely sensed as an R-wave from the ventricular sensing signal. The techniques disclosed herein enable IMD 14 to detect evidence of oversensing when it occurs and/or evidence indicating that oversensing may be likely to occur and take corrective action to reduce the likelihood of atrial event and/or H-wave (or bundle branch potential) oversensing by adjusting a ventricular sensing control parameter.

Figure 3:
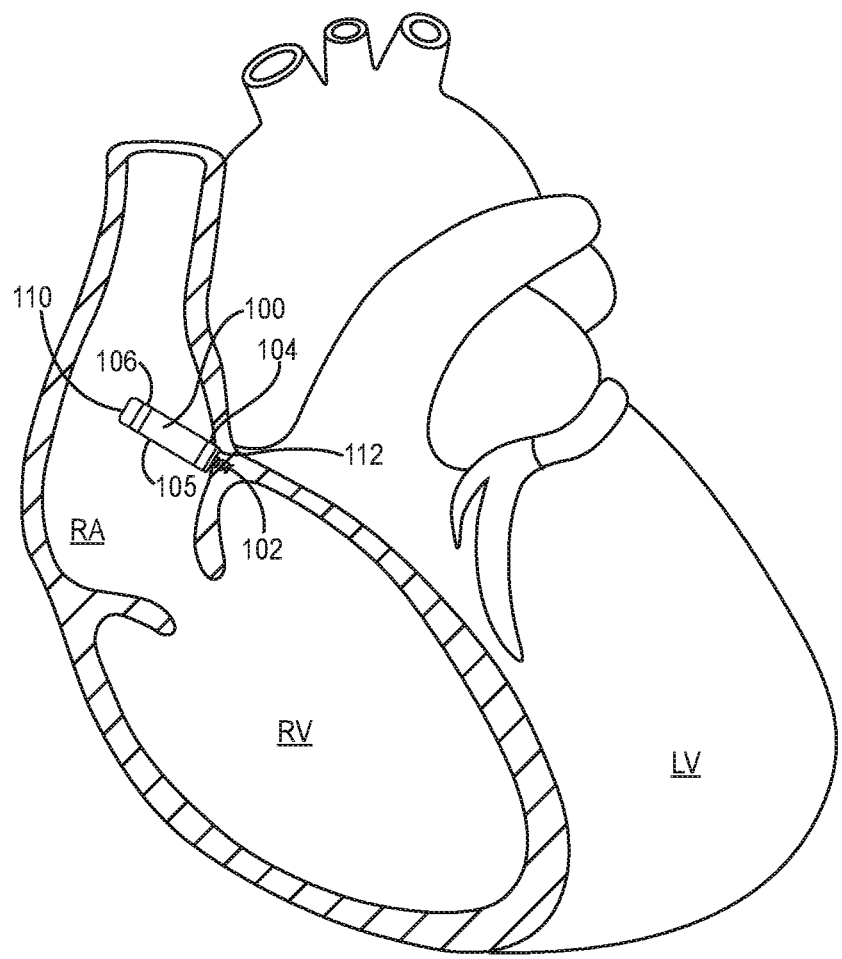
FIG. 3 is a conceptual diagram of a leadless intracardiac pacemaker positioned within the right atrium for providing ventricular pacing via the His bundle.

FIG. 3 is a conceptual diagram of a leadless intracardiac pacemaker 100 positioned within the RA for providing ventricular pacing via the His bundle. Pacemaker 100 may include a distal tip electrode 102 extending away from a distal end 112 of the pacemaker housing 105. Intracardiac pacemaker 100 is shown implanted in the RA of the patient's heart 8 to place distal tip electrode 102 for delivering pacing pulses to the His bundle. For example, the distal tip electrode 102 may be inserted into the inferior end of the interatrial septum, beneath the AV node and near the tricuspid valve annulus to position tip electrode 102 in, along or proximate to the His bundle. Distal tip electrode 102 may be a helical electrode providing fixation to anchor the pacemaker 100 at the implant position. In other examples, pacemaker 100 may include a fixation member that includes one or more tines, hooks, barbs, helices or other fixation member(s) that anchor the distal end of the pacemaker 100 at the implant site.

A portion of the distal tip electrode 102 may be electrically insulated such that only the most distal end of tip electrode 102, furthest from housing distal end 112, is exposed to provide targeted pacing at a tissue site that includes a portion of the His bundle. One or more housing-based electrodes 104 and 106 may be carried on the surface of the housing of pacemaker 100. Electrodes 104 and 106 are shown as ring electrodes circumscribing the longitudinal sidewall of pacemaker housing 105 extending from distal end 112 to proximal end 110. In other examples, a return anode electrode used in sensing and pacing may be positioned on housing proximal end 110. Pacing of the ventricles, e.g., via the His-Purkinje system, may be achieved using the distal tip electrode 102 as the cathode electrode and either of the housing-based electrodes 104 and 106 as the return anode.

Cardiac electrical signals produced by heart 8 may be sensed by pacemaker 100 using a sensing electrode pair selected from electrodes 102, 104 and 106. For example, a ventricular electrical signal for sensing ventricular R-waves may be sensed using distal tip electrode 112 and distal housing-based electrode 104. An atrial electrical signal for sensing atrial P-waves may be sensed using electrodes 104 and 106. The atrial and ventricular electrical signals may be analyzed for sensing atrial and ventricular events. In some examples, pacemaker 100 is a dual chamber pacemaker configured to deliver atrial pacing pulses using a housing based distal electrode 104 and proximal electrode 106 and deliver ventricular pacing pulses via tip electrode 102 and proximal electrode 106. Examples of dual chamber intracardiac pacemakers which may incorporate the techniques disclosed herein for controlling ventricular sensing parameters are generally disclosed in U.S. Patent Application Publication No. 2019/0083800 (Yang, et al.), incorporated herein by reference in its entirety.

The example IMD of FIGS. 1 and 2 and pacemaker 100 of FIG. 3 are illustrative examples of a medical device configured to accumulate evidence of actual or possible oversensing of atrial events and/or cardiac potential signals as false R-waves and control ventricular sensing according to the techniques disclosed herein. These techniques are not limited to the illustrative configurations of sensing and pacing devices and associated electrodes shown in FIGS. 1-3, however. In various examples, a medical device configured to perform the techniques disclosed herein may include a leadless device having housing-based electrodes (as shown in FIG. 3), a leadless pacemaker having an extension carrying one or more electrodes, or a medical device that is coupled to one or more medical electrical leads configured to position ventricular pacing and sensing electrodes. Such examples may include external pacemakers coupled to one or more transcutaneous medical electrical leads.

Figure 4:
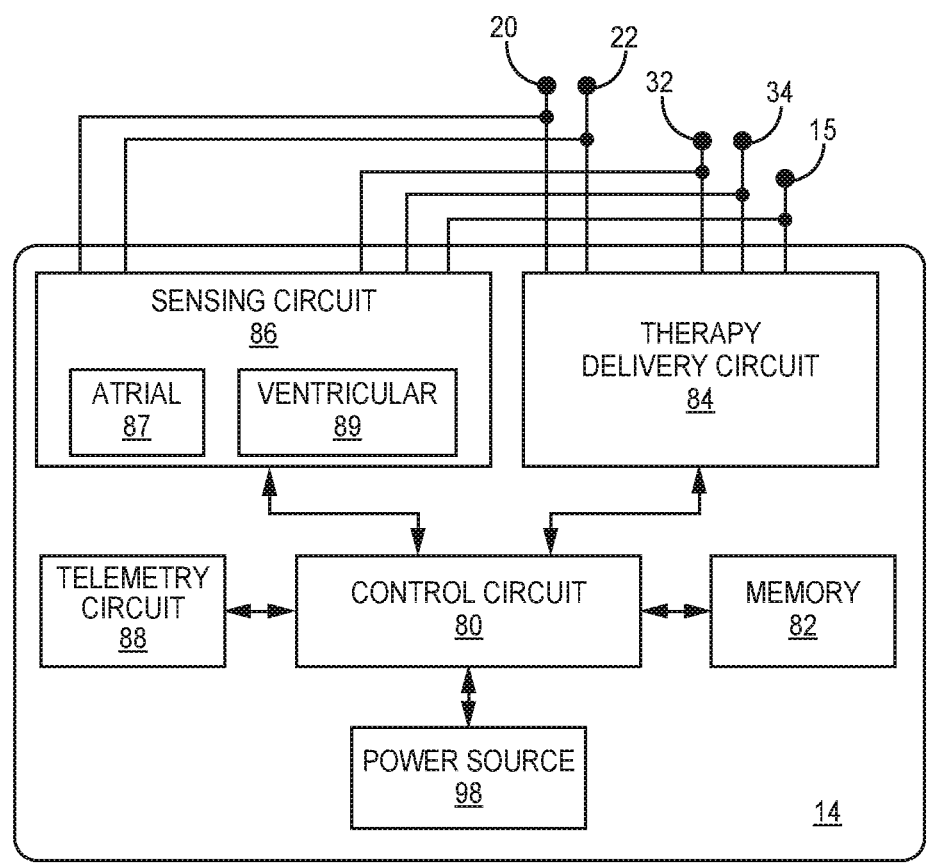
FIG. 4 is a schematic diagram of circuitry that may be enclosed within an IMD configured to perform sensing and pacing using techniques disclosed herein.

FIG. 4 is a schematic diagram of circuitry that may be enclosed within an IMD configured to perform sensing and pacing using techniques disclosed herein. The block diagram of FIG. 4 represents IMD 14 (FIGS. 1 and 2) for the sake of illustration. It is to be understood that the functionality attributed to the various circuits and components shown in FIG. 4 for performing ventricular pacing and sensing with monitoring for oversensing evidence may be similarly implemented in the intracardiac pacemaker 100 of FIG. 3 or other medical devices capable of delivering ventricular pacing pulses and sensing cardiac electrical signals.

Housing 15 is represented as an electrode in FIG. 4 for use in cardiac electrical signal sensing and, in some examples, for delivery of cardiac electrical stimulation pulses such as unipolar pacing pulses. The electronic circuitry enclosed within housing 15 includes software, firmware and/or hardware that cooperatively monitor cardiac electrical signals, determine when a pacing therapy is necessary, and deliver electrical pacing pulses to the patient's heart as needed according to programmed pacing mode and pacing pulse control parameters. The electronic circuitry includes a control circuit 80, memory 82, therapy delivery circuit 84, sensing circuit 86, telemetry circuit 88 and power source 98.

Power source 98 provides power to the circuitry of IMD 14 including each of the circuits 80, 82, 84, 86, and 88 as needed. Power source 98 may include one or more energy storage devices, such as one or more rechargeable or non-rechargeable batteries. The connections between power source 98 and each of the other components 80, 82, 84, 86, and 88 are to be understood from the general block diagram of FIG. 4 but are not shown for the sake of clarity. For example, power source 98 may be coupled to one or more charging circuits included in therapy delivery circuit 84 for providing the power needed to charge holding capacitors included in therapy delivery circuit 84 that are discharged at appropriate times under the control of control circuit 80 for generating and delivering pacing pulses. Power source 98 is also coupled to components of sensing circuit 86 (such as sense amplifiers, analog-to-digital converters, switching circuitry, etc.), telemetry circuit 88 and memory 82 to provide power to the various circuits as needed.

The functional blocks shown in FIG. 4 represent functionality included in IMD 14 and may include any discrete and/or integrated electronic circuit components that implement analog and/or digital circuits capable of producing the functions attributed to IMD 14 (or pacemaker 100) herein. The various components may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. Providing software, hardware, and/or firmware to accomplish the described functionality in the context of any modern cardiac medical device system, given the disclosure herein, is within the abilities of one of skill in the art.

Control circuit 80 communicates, e.g., via a data bus, with therapy delivery circuit 84 and sensing circuit 86 for sensing cardiac electrical signals and scheduling delivery of cardiac electrical stimulation therapies in response to sensed cardiac events, e.g., P-waves attendant to atrial depolarization and R-waves attendant to ventricular depolarization, or the absence thereof. The available electrodes are electrically coupled to therapy delivery circuit 84 for delivering electrical stimulation pulses to the patient's heart and/or to sensing circuit 86 for sensing cardiac electrical signals produced by the heart, which may include both intrinsic signals (such as intrinsic P-waves and R-waves) produced by the heart in the absence of a pacing pulse that captures the heart and evoked response signals produced by the heart in response to a delivered pacing pulse of sufficient energy to cause capture.

Sensing circuit 86 may include cardiac event detection circuitry, which may include one or more sense amplifiers, filters, rectifiers, threshold detectors, comparators, analog-to-digital converters (ADCs), timers or other analog or digital components, for detecting cardiac electrical events. Sensing circuit 86 may include two or more sensing channels for detecting cardiac electrical events from two or more sensing electrode vectors. Sensing circuit 86 may include switching circuitry for selectively coupling a sensing electrode pair from the available electrodes to the atrial channel 87 and the ventricular channel 89. Switching circuitry may include a switch array, switch matrix, multiplexer, or any other type of switching device suitable to selectively couple components of sensing circuit 86 to selected electrodes. For example, an atrial signal may be received by atrial channel 87 via electrodes 20 and 22 of atrial lead 16 (FIG. 1), and a ventricular signal may be received by ventricular channel 89 via electrodes 32 and 34 of ventricular lead (FIGS. 1 and 2).

An atrial event detector may be included in atrial channel 87 for detecting intrinsic P-waves attendant to intrinsic atrial depolarizations using one or both of electrodes 20 and 22 carried by RA lead 16. A ventricular event detector may be included in ventricular channel 89 for detecting intrinsic R-waves attendant to intrinsic ventricular depolarizations using one or both electrodes 32 and 34 carried by ventricular lead 18. A cardiac event sensing threshold, such as a P-wave sensing threshold or an R-wave sensing threshold, may be automatically adjusted by sensing circuit 86 under the control of control circuit 80, e.g., based on timing intervals and sensing threshold values determined by control circuit 80, stored in memory 82, and/or controlled by hardware, firmware and/or software of control circuit 80 and/or sensing circuit 86. The R-wave sensing threshold, for example, may be controlled to start at a starting threshold voltage (which may be based on a previously sensed R-wave amplitude) following a post-ventricular blanking period then decrease according to a decay profile until reaching a minimum sensing threshold. The minimum R-wave sensing threshold may be set to a programmed sensitivity setting of the ventricular channel. The sensitivity setting, programmed to a voltage level typically in millivolts, e.g., in the range of 0.3 millivolts to 1.8 millivolts, is the lowest voltage level above which an R-wave is sensed by the ventricular channel, which may be a true R-wave or a falsely sensed R-wave, e.g., due to a P-wave or H-wave crossing the R-wave sensing threshold.

Upon detecting a cardiac electrical event based on a sensing threshold crossing, sensing circuit 86 may produce a sensed event signal that is passed to control circuit 80. For example, an atrial event detector of atrial channel 87 may produce a P-wave sensed event signal in response to a P-wave sensing threshold crossing that occurs outside any applied atrial blanking periods. A ventricular event detector of ventricular channel 89 may produce an R-wave sensed event signal in response to an R-wave sensing threshold crossing. The sensed event signals produced by sensing circuit 86 are used by control circuit 80 for inhibiting a scheduled pacing pulse and/or for setting pacing escape interval timers that control the basic time intervals used for scheduling cardiac pacing pulses.

As described below in conjunction with FIG. 5, the ventricular channel may also include an oversense event detector that is configured to detect the time of an R-wave sensing threshold crossing that may occur during a post-atrial time interval. The post-atrial time interval may be started in response to a P-wave sensed event signal produced by atrial channel 87 or an atrial pacing pulse generated by therapy delivery circuit 84. The time of an R-wave sensing threshold crossing during the post-atrial time interval may be used by control circuit 80 for accumulating oversensing evidence, even when the R-wave sensing threshold crossing during the post-atrial time interval is not sensed by the ventricular event detector, e.g., due to a post-atrial ventricular blanking period, such that an R-wave sensed event signal is not produced by sensing circuit 86. In this way and as further described below, sensing circuit 86 and control circuit 80 are configured to cooperatively detect and accumulate evidence of possible oversensing whether or not actual oversensing of atrial events or other events such as H-waves as false R-waves is occurring.

Each of atrial channel 87 and the ventricular channel 89 may also produce a respective digital electrogram (EGM) signal that may be passed to control circuit 80 for further processing and analysis. Each channel 87 and 89 may include an input filter for receiving the atrial or ventricular signal from a respective pair of sensing electrodes, a pre-amplifier, an analog-to-digital converter and a bandpass, low pass or high pass filter for producing the multi-bit digital EGM signals that may be passed to control circuit 80. Control circuit 80 may analyze the ventricular EGM signal in some examples for accumulating oversensing evidence.

Control circuit 80 may determine ventricular signal features, such as a maximum peak signal amplitude, time of the maximum peak, and/or R-wave sensing threshold crossing time during a post-atrial time interval, based on signals received from the oversense event detector of ventricular channel 89 and/or by processing and analysis of the ventricular EGM signal received from ventricular channel 89. Such ventricular signal features may be used by control circuit 80 for accumulating oversensing evidence and controlling ventricular sensing control parameters based on that evidence.

Control circuit 80 may include various timers or counters for counting down various pacing escape intervals, e.g., an atrioventricular (AV) pacing interval, a VV pacing interval, an AA pacing interval, etc. A sensed event signal may trigger or inhibit a pacing pulse depending on the particular programmed pacing mode. For example, a P-wave sensed event signal received from sensing circuit 86 may cause control circuit 80 to inhibit a scheduled atrial pacing pulse and schedule a ventricular pacing pulse at a programmed AV pacing interval. If the AV pacing interval expires before control circuit 80 receives an R-wave sensed event signal from sensing circuit 86, control circuit 80 may control therapy delivery circuit 84 to deliver a ventricular pacing pulse at the AV pacing interval following the sensed P-wave and in this way deliver atrial-synchronized ventricular pacing. If an R-wave sensed event signal is received from sensing circuit 86 before the AV pacing interval expires, the scheduled ventricular pacing pulse may be inhibited. The AV pacing interval controls the amount of time between an atrial event, paced or sensed, and a ventricular pacing pulse to promote AV synchrony in an atrial tracking ventricular pacing mode. However, when an event, which may be an atrial pacing pulse artifact, atrial evoked response signal, intrinsic P-wave, or H-wave, is oversensed as a false R-wave by the ventricular event detector of ventricular channel 89, a ventricular pacing pulse may be withheld resulting in a ventricular pause or ventricular asystole in a pacemaker-dependent patient.

Accordingly, control circuit 80 is configured to accumulate actual and/or possible oversensing evidence using the techniques disclosed herein for controlling R-wave sensing by ventricular channel 89 in a manner that avoids or minimizes the likelihood of actual oversensing of atrial events and/or cardiac potential signals as false R-waves. For example, control circuit 80 may include a counter for counting event time signals produced by sensing circuit 86 that correspond to an R-wave sensing threshold crossing during a post-atrial time interval. The event time signals may be produced by an oversense event detector included in sensing circuit 86 as further described below. Oversensing evidence may be accumulated by control circuit 80 by at least counting the number of event time signals produced during post-atrial time intervals, e.g., over a moving predetermined number of ventricular cycles.

A medical device configured to perform the techniques disclosed herein may be configured for delivering ventricular bradycardia pacing therapy, atrial synchronized ventricular pacing, rate responsive pacing, cardiac resynchronization therapy (CRT), anti-tachycardia pacing therapy or other pacing therapies which may include pacing the ventricles, e.g., via the His-Purkinje system or any portion thereof. Therapy delivery circuit 84 may include charging circuitry, one or more charge storage devices such as one or more holding capacitors, an output capacitor, and switching circuitry that controls when the holding capacitor(s) are charged and discharged across the output capacitor to deliver a pacing pulse to a selected pacing electrode vector coupled to the therapy delivery circuit 84. Therapy delivery circuit 84 may include one or more pacing channels. In the example of IMD 14, therapy delivery circuit 84 may include an atrial pacing channel and a ventricular pacing channel. Each pacing channel may include one or more holding capacitors, one or more switches, and an output signal line, which may include at least one output capacitor, for producing pacing pulses delivered by the respective atrial lead 16 (electrodes 20 and 22) or ventricular lead 18 (electrodes 32 and 34). Charging of a holding capacitor to a programmed pacing voltage amplitude and discharging of the capacitor for a programmed pacing pulse width may be performed by therapy delivery circuit 84 according to control signals received from control circuit 80. For example, a pace timing circuit included in control circuit 80 may include programmable digital counters set by a microprocessor of the control circuit 80 for controlling the basic pacing time intervals associated with various single chamber or dual chamber pacing modes, CRT or anti-tachycardia pacing sequences. The microprocessor of control circuit 80 may also set the amplitude, pulse width, polarity or other characteristics of the cardiac pacing pulses, which may be based on programmed values stored in memory 82.

In some examples, IMD 14 may be configured to detect non-sinus tachycardia and deliver anti-tachycardia pacing (ATP). Control circuit 80 may determine cardiac event time intervals, e.g., PP intervals between consecutive P-wave sensed event signals received from sensing circuit 86 and/or RR intervals between consecutive R-wave sensed event signals received from sensing circuit 86. These intervals may be compared to tachycardia detection intervals for detecting non-sinus tachycardia. Tachycardia may be detected in a given heart chamber based on a threshold number of tachycardia detection intervals being detected. In response to detecting atrial or ventricular tachycardia, control circuit 80 may control therapy delivery circuit 84 to deliver ATP.

In some examples, therapy delivery circuit 84 may include high voltage therapy circuitry for generating high voltage shock pulses in addition to low voltage therapy circuitry for generating low voltage pacing pulses. In response to detecting atrial or ventricular tachycardia or fibrillation, control circuit 80 may control therapy delivery circuit 84 to deliver a cardioversion/defibrillation (CV/DF) shock. The high voltage therapy circuitry may include high voltage capacitors and high voltage charging circuitry for generating and delivering CV/DF shock pulses.

Control parameters utilized by control circuit 80 for sensing cardiac events and controlling pacing therapy delivery may be programmed into memory 82 via telemetry circuit 88. Telemetry circuit 88 includes a transceiver and antenna for communicating with an external device 50 as described above in conjunction with FIG. 1 using radio frequency communication or other communication protocols. Under the control of control circuit 80, telemetry circuit 88 may receive downlink telemetry from and send uplink telemetry to the external device 50. In some cases, telemetry circuit 88 may be used to transmit and receive communication signals to/from another medical device implanted in the patient.

Figure 5:
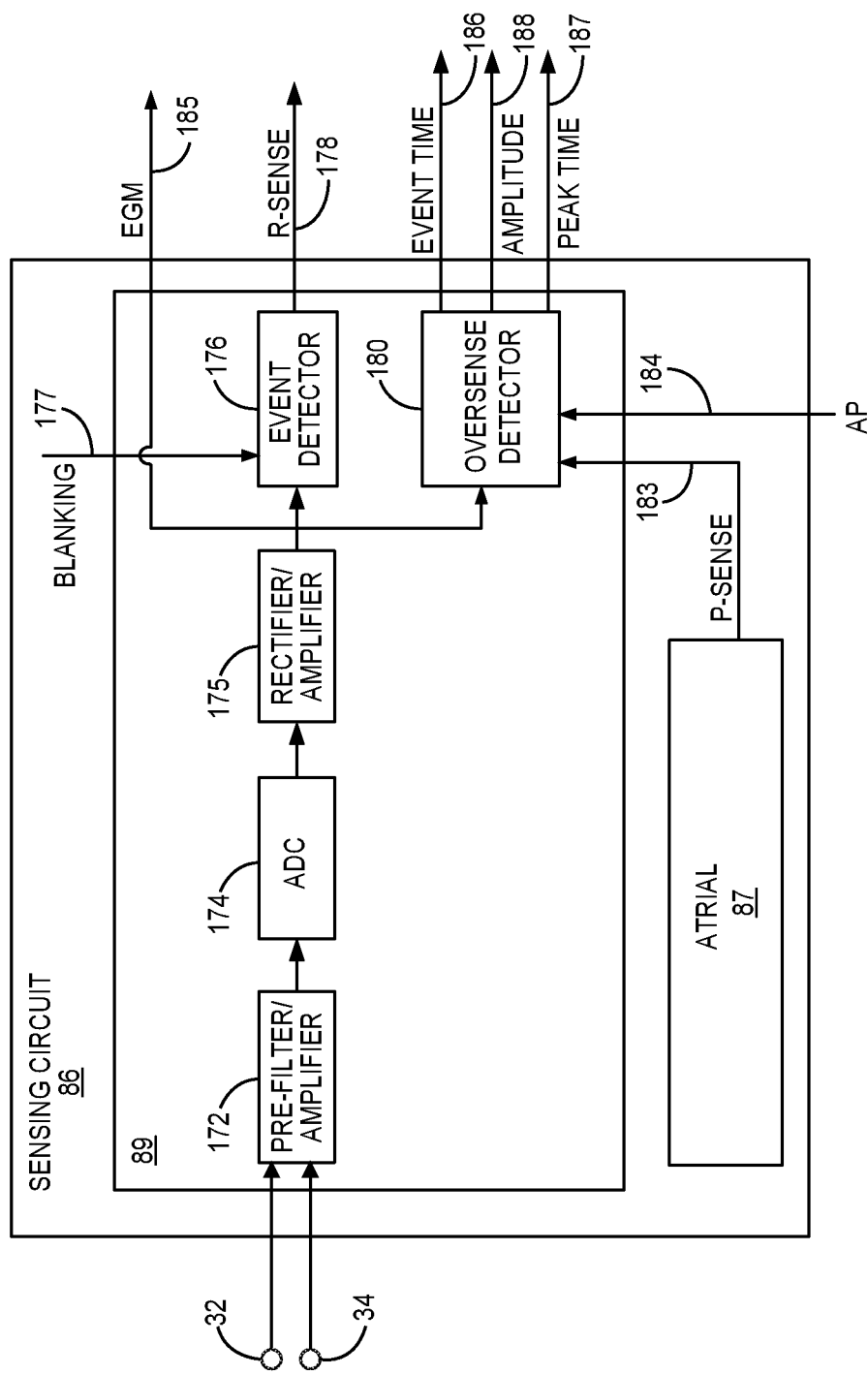
FIG. 5 is a schematic diagram of circuitry that may be included in the ventricular channel of the sensing circuit shown in FIG. 4.

FIG. 5 is a conceptual diagram of circuitry that may be included in the ventricular channel 89 of sensing circuit 86 shown in FIG. 4. In this example, ventricular channel 89 includes a pre-filter/amplifier 172, an analog to digital convertor (ADC) 174, a rectifier/amplifier 175, and a ventricular event detector 176. The pre-filter amplifier circuit 172 receives a ventricular signal from ventricular pacing and sensing electrodes 32 and 34 (or from one of electrodes 32 or 34 paired with housing 15). It is recognized that in other configurations other available electrodes may be selected for receiving a ventricular electrical signal produced by the patient's heart. Pre-filter/amplifier circuit 172 may include a low pass filter for filtering out high frequency noise or artifact and amplifies the filtered signal, which is passed to ADC 174. ADC 174 passes a digitized signal to rectifier/amplifier circuit 175 which may include a rectifier, band pass filter, and/or amplifier for passing a rectified signal to ventricular event detector 176.

Ventricular event detector 176 may include a comparator, sense amplifier or other detection circuitry configured to detect an R-wave sensing threshold crossing by the ventricular signal. In response to an R-wave sensing threshold crossing, ventricular event detector 176 produces an R-wave sensed event signal 178 that is output to control circuit 80. Ventricular event detector 176 may receive a blanking signal 177, which may be controlled by timers in sensing circuit 86 or control circuit 80 and set according to sensing control parameters received from control circuit 80. As described below, control circuit 80 may enable a post-atrial ventricular blanking period in response to accumulated oversensing evidence in order to reduce the likelihood of oversensing atrial events and/or a cardiac potential signal of the His bundle or bundle branches. For example, ventricular event detector 176 may apply the post-atrial blanking interval to the ventricular signal received from rectifier/amplifier 175 to prevent ventricular event detector 176 from producing an R-wave sensed event signal 178 during the post-atrial ventricular blanking interval. Ventricular event detector 176 is prevented from producing a false R-wave sensed event signal based on an R-wave sensing threshold crossing that may occur during the post-atrial ventricular blanking period. In other examples, the post-atrial blanking period may be applied by control circuit 80 to ignore any R-wave sensed event signals produced by ventricular event detector 176 and received during the post-atrial blanking period.

Blanking signal 177 may set a start time and a duration or end time for blanking the ventricular event detector 176 during a blanking period started in response to an atrial event, sensed or paced. In some examples, blanking signal 177 received by event detector 176, or more generally ventricular channel 89, may include multiple blanking signals that are applied to one or more components of ventricular channel 89 such that event detector 176 is effectively disabled from sensing events during the post-atrial blanking period and is re-enabled to sense events upon termination of the post-atrial blanking period. In various examples, the blanking period may be applied by temporarily disabling or powering down circuitry of ventricular channel 89 or otherwise inhibiting event detector 176 from generating R-wave sensed event signals during the post-atrial ventricular blanking period.

In some examples, ventricular channel 89 may include an oversense event detector 180 which may include a comparator, sense amplifier, or other detection circuitry that detects an R-wave sensing threshold crossing of the ventricular signal received from rectifier/amplifier 175. Oversense event detector 180 may receive input from rectifier amplifier circuit 175. Oversense event detector 180 may include the same or similar circuitry as ventricular event detector 176 configured to detect an R-wave sensing threshold crossing. In other examples, oversense event detector 180 may receive input from ADC 174 and include a rectifier/amplifier circuit, which may be the same or similar to rectifier/amplifier circuit 175. In various examples, the input to the oversense event detector 180 may be received from electrodes 32 and 34 directly or from any point in pre-filter/amplifier 172, ADC 174, rectifier/amplifier circuit 175 or ventricular event detector 176. As such, oversense event detector 180 may include circuitry for filtering, amplifying, digitizing and/or rectifying as needed depending on the input source. One or both of ventricular event detector 176 or oversense event detector 180 may include a peak amplitude detector circuit for detecting the peak amplitude and/or time of the peak amplitude of a cardiac electrical signal event that crosses a respective R-wave sensing threshold.

Oversense event detector 180, however, does not apply the post-atrial ventricular blanking period when it is enabled and applied by ventricular event detector 176 (or control circuit 80). Instead, oversense event detector 180 may be enabled to sense R-wave sensing threshold crossings that occur during the post-atrial ventricular blanking period. Oversense event detector 180, however, does not produce R-wave sensed event signals in response to an R-wave sensing threshold crossing. Instead, oversense event detector 180 may pass an event time signal 186 and, at least in some examples, an event peak amplitude signal 188 determined from the event signal that crossed the R-wave sensing threshold to control circuit 80.

In some examples, oversense event detector 180 may generate an event time signal 186 corresponding to an R-wave sensing threshold crossing, where the event time signal 186 coincides with the time of the detected R-wave sensing threshold crossing. Additionally or alternatively, oversense event detector 180 may generate an event time signal that coincides with the time of the peak amplitude of the event signal that crossed the R-wave sensing threshold. An event time signal coinciding with the peak amplitude corresponding to an R-wave sensing threshold is shown in FIG. 5 as peak time signal 187. The peak time signal 187 may be the time of the maximum peak amplitude of the rectified cardiac electrical signal detected during a post-atrial time interval. The maximum peak amplitude may be detected following an R-wave sensing threshold crossing during the post-atrial time interval. The post-atrial time interval may be the same or different than the post-atrial ventricular blanking period applied by event detector 176.

In various examples described herein, one or both of event time signal 186 and peak time signal 187 may be passed to control circuit 80. Control circuit 80 accumulates oversensing evidence based on the event time signal 186, peak time signal 187, and/or event amplitude signal 188. In other examples, control circuit 80 may receive a digitized ventricular EGM signal 185 from ventricular channel 89 and process and analyze the EGM signal 185 for detecting and determining oversensing evidence, such as for determination of an R-wave sensing threshold crossing time following an atrial event and/or the maximum peak amplitude and peak time of the EGM signal following an atrial event or following event time signal 186.

In some examples, oversense event detector 180 may receive a P-wave sensed event signal 183 from atrial channel 87 indicating the timing of a sensed P-wave. Alternatively, atrial channel 87 may pass a P-wave sensed event signal to control circuit 80 each time a P-wave sensing threshold is crossed, and control circuit 80 may pass the P-wave sensed event signal 183 to oversense event detector 180. Oversense event detector 180 may additionally receive an atrial pace signal 184 (from therapy delivery circuit 84 or from control circuit 80) indicating the time that an atrial pacing pulse is generated and delivered by therapy delivery circuit 84.

Oversense event detector 180 may be configured to detect when an R-wave sensing threshold crossing of the ventricular signal occurs during a post-atrial time interval extending from a P-wave sensed event signal or from an atrial pacing pulse. The post-atrial time interval may correspond to the post-atrial ventricular blanking period that may be applied by ventricular event detector 176. In other examples, the post-atrial time interval may be a programmable time interval that may start and/or end at different times than the post-atrial ventricular blanking period. For instance, the post-atrial time interval may be longer than the post-atrial ventricular blanking period. As an example, the post-atrial ventricular blanking period may be set to 80 milliseconds (ms) and the post-atrial time interval may be set to 120 ms. Oversense event detector 180 may be enabled to detect R-wave sensing threshold crossings only during the post-atrial time interval in order to generate an event time signal 186 (and/or a peak time signal 187 and/or event peak amplitude signal 188 in some examples) that is received by control circuit 80 for use in accumulating oversensing evidence.

In this way, oversensing evidence indicating the likelihood of falsely sensing atrial events and/or cardiac potential signals by ventricular event detector 176 may be accumulated even when false R-wave sensed event signals are not being produced by ventricular event detector 176. For instance, R-wave sensing threshold crossings may be detected by oversense event detector 180 during an overlapping portion of the post-atrial time interval and the post-atrial ventricular blanking period. Oversense event detector 180 may produce an event time signal 186 without an R-wave sensed event signal 178 being produced by ventricular event detector 176. Oversensing evidence may be increased based on the event time signal 186 without an atrial event or cardiac potential signal actually being oversensed by ventricular event detector 176 or used by control circuit 80 for inhibiting a ventricular pacing pulse.

Oversense event detector 180 may be controlled to detect R-wave sensing threshold crossings by the cardiac electrical signal when the R-wave sensing threshold is set to the same amplitude (which may decay over time) as the R-wave sensing threshold used by ventricular event detector 176. In this way, oversense event detector 180 may identify events that would be sensed by ventricular event detector 176 when post-atrial ventricular blanking is disabled. However, in other examples, oversense event detector 180 may be controlled to detect R-wave sensing threshold crossings when the R-wave sensing threshold is set differently (e.g., higher or lower) than the R-wave sensing threshold applied by ventricular event detector 176. For example, the oversense event detector 180 may be set to a different amplitude to determine how often events would be sensed (or not sensed) using a different R-wave sensing threshold than ventricular event detector 176. For instance, when the R-wave sensing threshold applied by oversense event detector 180 is lower than the R-wave sensing threshold applied by ventricular event detector 176, control circuit 80 may determine the likelihood of oversensing events during the post-atrial time interval by ventricular event detector 176 if the R-wave sensing threshold were reduced. Control circuit 80 may adjust the R-wave sensing threshold used by oversense event detector 180 to be different than the R-wave sensing threshold applied by ventricular event detector 176 temporarily to test a possible ventricular sensing control parameter, e.g., a sensitivity setting, in order to predict if oversensing is expected to occur prior to actually adjusting the ventricular sensing control parameter.

Figure 6:
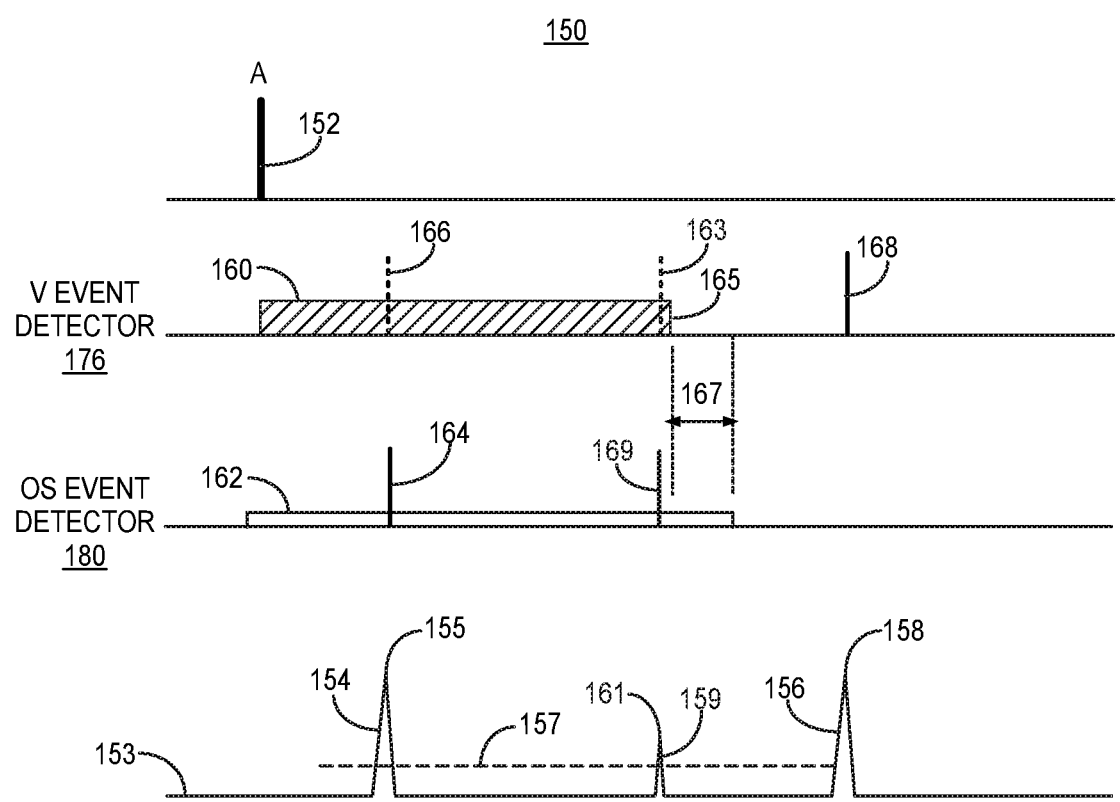
FIG. 6 is a timing diagram illustrating signals that may be generated by the ventricular channel of FIG. 5.

FIG. 6 is a timing diagram 150 illustrating signals that may be generated by ventricular event detector 176 and oversense event detector 180 of FIG. 5. An atrial event signal 152 may be received by ventricular channel 89 for use in setting the post-atrial blanking period 160 applied by ventricular event detector 176 (when blanking is enabled) and the post-atrial time interval 162 applied by oversense event detector 180. The atrial event signal 152 may correspond to an intrinsic P-wave sensed by sensing circuit 86 or an atrial pacing pulse generated by therapy delivery circuit 84.

A ventricular signal 153 represents the rectified signal passed from rectifier/amplifier 175 to ventricular event detector 176 and to oversense event detector 180. The ventricular signal 153 includes an early event signal 154 and a late event signal 156. The early event signal 154, occurring within the post-atrial time interval 162, is likely an atrial event signal corresponding to atrial event 152, which may be oversensed by ventricular event detector 176 if post-atrial ventricular blanking period 160 is disabled. If blanking period 160 is disabled, ventricular event detector 176 may generate a false R-wave sensed event signal 166, which may cause therapy delivery circuit 84 to withhold a ventricular pacing pulse. When post-atrial ventricular blanking 160 is enabled, however, any R-wave sensing threshold crossings that occur during post-atrial ventricular blanking period 160 are ignored by ventricular event detector 176 such that no R-wave sensed event signal is generated. In other examples, ventricular event detector 176 may generate the R-wave sensed event signal 166 during the blanking period 160, but control circuit 80 applies blanking period 160 and ignores any R-wave sensed event signals received during the blanking period 160 for the purposes of controlling ventricular pacing (e.g., no withholding or scheduling of a ventricular pacing pulse based on the R-wave sensed event signal 166).

Oversense event detector 180 is enabled to detect R-wave sensing threshold crossings during the post-atrial time interval 162. Oversense event detector 180 may be disabled or blanked after the expiration of post-atrial time interval 162 until the next atrial event that causes a new post-atrial time interval to be started. In this way, oversense event detector 180 may only generate an event time signal, e.g., event time signal 164, during the post-atrial time interval 162. The post-atrial time interval 162 may be set to a first duration, e.g., 80 ms, in response to the atrial event 152 being a sensed P-wave, e.g., in response to a P-wave sensed event signal 183 (FIG. 5) received from atrial channel 87 (or control circuit 80). The post-atrial time interval 162 may be set to a second duration that is longer than the first duration, e.g., 110 ms, when the atrial event 152 is an atrial pacing pulse. An atrial event signal 154 present in ventricular signal 153 may occur relatively later after an atrial pacing pulse than after a sensed P-wave due to the delay between the delivered pacing pulse and the electrical depolarization of the atrial myocardial tissue.

When ventricular signal 153 crosses R-wave sensing threshold 157 during the post-atrial time interval 162, oversense event detector 180 produces event time signal 164 that is used by control circuit 80 to accumulate oversensing evidence, e.g., as a count of event time signals produced by oversense event detector 180. The event time signal 164 may be ignored by control circuit 80 in controlling ventricular pacing or determining a ventricular rate or rhythm. For example, control circuit 80 may accumulate oversense evidence by increasing the value of an oversense event counter each time an event time signal 164 is received from oversense event detector 180. Control circuit 80 may use the accumulated oversense evidence, e.g., the value of the oversense event counter, to determine whether oversensing criteria are met based on the number of event time signals produced by oversense event detector 180 (within the post-atrial time interval) over a predetermined number of ventricular cycles. When oversensing criteria are met, oversensing by ventricular event detector 176 is highly likely if post-atrial ventricular blanking period 160 is disabled, given the currently programmed ventricular sensitivity setting, and any other sensing threshold control parameters, used to control R-wave sensing threshold 157.

Control circuit 80 uses event time signal 164 in controlling ventricular sensing control parameters that are applied to ventricular event detector 176, such as enabling or disabling post-atrial ventricular blanking period 160, setting the end time 165 of post-atrial ventricular blanking period 160 (e.g., based on the timing of event time signal 164 following atrial event 152), and/or adjusting the ventricular sensitivity setting that is used in controlling R-wave sensing threshold 157. The R-wave sensing threshold 157 shown in FIG. 6 may be equal to the ventricular sensitivity setting which is the sensing floor or lowest voltage amplitude that an auto-adjusting R-wave sensing threshold is adjusted to. R-wave sensing threshold 157 may be set to a starting value following a ventricular pacing pulse or sensed R-wave and be decreased according to one or more decay rates or step drops to the ventricular sensitivity setting, e.g., to 0.075, 0.1. 0.3. 0.45, 0.6, 0.9, or 1.2 millivolts or other programmed value. As described below, control circuit 80 may be configured to adjust the ventricular sensitivity setting, end time 165 of the post-atrial ventricular blanking period 160 and/or enable or disable the post-atrial ventricular blanking period 160 based on oversensing evidence accumulated in response to receiving event signals from oversense event detector 180, such as event time signal 164. In addition to the event time signal 164 indicating the time of an R-wave sensing threshold crossing during a post-atrial time interval 162, oversense event detector 180 may include a peak detector for determining the maximum peak amplitude 155 of the event 154 that crossed R-wave sensing threshold 157 as well as the time of the peak amplitude 155. Oversense event detector 180 may generate an amplitude signal (signal 188, FIG. 5) indicating the maximum peak amplitude 155 and/or a peak time signal (signal 187, FIG. 5). As described below, the maximum peak amplitude 155 may be used by control circuit 80, in addition to other accumulated oversensing evidence, for determining whether or not to adjust the ventricular sensitivity setting and/or enable post-atrial ventricular blanking period 160 to reduce the likelihood of oversensing by ventricular channel 89. The time of the maximum peak may be used to set the ending time of the post-atrial ventricular blanking period 160 in some examples.

In some examples, a cardiac potential signal 159 may be present in the ventricular signal 153. Cardiac potential signal 159 may be a His bundle potential signal or H-wave and may occur, for example, 30 to 70 ms after the atrial event 152 and 20 to 50 ms before a true R-wave. The potential signal 159 may occur during the post-atrial time interval 162 causing oversense event detector 180 to generate an event time signal 169, indicating the time of an R-wave sensing threshold crossing that could potentially be an oversensed signal if post-atrial ventricular blanking period 160 is disabled or shortened. Ventricular event detector 176 does not generate an R-wave sensed event signal 163 (as indicated by dashed line) when the ventricular blanking period 160 is enabled and expires later than the time of the cardiac potential signal 159.

Oversense event detector 180 may generate an amplitude signal indicating the maximum peak amplitude 161 of potential signal 159. As described above, oversense event detector 180 may additionally or alternatively generate a peak time signal indicating the time of the maximum peak 161 of the potential signal 159. Control circuit 80 may accumulate oversensing evidence in response to receiving the event time signal 169 (and/or peak amplitude and/or peak time signals) and use the accumulated oversensing evidence and/or event amplitude information to adjust ventricular sensing control parameters, e.g., by increasing the ventricular sensitivity setting to be greater than the amplitude of the potential signal 159, and/or enable or extend post-atrial ventricular blanking period 160 to expire later than the time of the potential signal 159 after the atrial event 152. Control circuit 80 may adjust the duration or ending time of post-atrial time interval 162 based on the timing of the latest event time signal 159 occurring during the post-atrial time interval 162. In various examples, an oversense event time may be determined from an atrial event signal to the latest event time signal during the post-atrial time interval 162 for each one of multiple cardiac cycles. The ending time of post-atrial ventricular blanking period 160 and/or the post-atrial time interval 162 may be adjusted based on a metric of the oversense event times, e.g., based on the mean, median, nth longest, longest or other metric of the timing of the latest event time signals over one or more cardiac cycles.

While both an early signal 154 which may correspond to an atrial event 152 and a potential signal 159 are shown in the ventricular signal 153, it is recognized that in various instances one, both or neither of the signals 154 and 159 may be present in the ventricular signal 153 for a given cardiac cycle. When two or more signals cross the R-wave sensing threshold 157 during post-atrial time interval 162, control circuit 80 may accumulate oversense evidence, e.g., as a count of event time signals, in response to only one signal or all event time signals generated by oversense event detector 180 during a given cardiac cycle. In the example of FIG. 6, control circuit 80 may accumulate oversense evidence, e.g., by increasing an oversense event counter by one, in response to only one event time signal 164 or 169, or increase the oversense evidence counter by two, in response to each event time signal 164 and 169.

The late event 156 of ventricular signal 153 crosses the R-wave sensing threshold 157. The R-wave sensing threshold 157 may be equal to the ventricular sensitivity setting at this point in time in the ventricular cycle since the earlier events 154 and 159 were not sensed by ventricular event detector 176 and not used in resetting the R-wave sensing threshold amplitude to a starting value based on a sensed event amplitude. The late event 156 occurs outside the post-atrial ventricular blanking period 160 and after the post-atrial time interval 162. The ventricular event detector 176 generates an R-wave sensed event signal 168 that is used by control circuit 80 in controlling ventricular pacing, e.g., inhibiting a scheduled ventricular pacing pulse and/or starting a ventricular lower rate pacing interval. The oversense event detector 180 may be disabled or may not receive the ventricular signal 153 outside the post-atrial time interval 162. As such, oversense event detector 180 does not generate an event time signal in response to event 156 crossing R-wave sensing threshold 157.

In some examples, control circuit 80 may determine the peak amplitude 158 of late events, such as event 156, that cause ventricular event detector 176 to produce an R-wave sensed event signal 168. The peak amplitude 158 may be used by control circuit 80 in determining an R-wave amplitude metric. As described below, an R-wave amplitude metric may be used in determining whether or not to adjust the ventricular sensitivity setting when oversensing evidence criteria are met. In other examples, ventricular event detector 176 may include a peak detector circuit and be configured to detect the peak amplitude 158 of the late event 156 associated with an R-wave sensed event signal 168. Ventricular event detector 176 may generate a peak amplitude signal that is passed to control circuit 80 indicating the amplitude (e.g., in volts or millivolts) of late event 156. In still other examples, the peak detector implemented in oversense event detector 180 may be enabled to determine the peak amplitude of both early and late events, both within and outside the post-atrial time interval 162, so that oversense event detector 180 may pass a peak amplitude signal to control circuit 80 indicating the peak amplitude 158 of the late event 156.

It is to be understood that, while FIGS. 4 and 5 depict one example configuration of the circuitry implemented for detecting R-wave sensing threshold crossings and generating associated time and amplitude signals for accumulating oversensing evidence and adjusting ventricular sensing control parameters, the functionality disclosed herein may be implemented in a variety of configurations in which one or more circuits and/or processors are configured to cooperatively perform the functionality described and attributed herein to IMD 14 or pacemaker 100.

When post-atrial ventricular blanking 160 is disabled, an R-wave sensing threshold crossing during (or after) the post-atrial time interval 162 causes ventricular event detector 176 to produce an R-wave sensed event signal (e.g., 163, 166 or 168). Control circuit 80 withholds a scheduled ventricular pacing pulse in response to receiving the R-wave sensed event signal. The ventricular pacing pulse may be scheduled at the expiration of an AV pacing interval or a VV pacing interval. When post-atrial ventricular blanking is enabled, only an R-wave sensing threshold crossing outside the post-atrial ventricular blanking period 160, e.g., event 156, may cause control circuit 80 to withhold a scheduled ventricular pacing pulse. The R-wave sensing threshold crossing may or may not occur within the post-atrial time interval 162. For instance, when post-atrial time interval 162 is longer than the post-atrial blanking period 160, ventricular event detector 176 may produce an R-wave sensed event signal in response to an R-wave sensing threshold crossing by ventricular signal 153 during a non-overlapping portion 167 of post-atrial time interval 162 and post-atrial blanking period 160. The R-wave sensed event signal may cause control circuit 80 to withhold a scheduled ventricular pacing pulse. Oversense event detector 180 may produce an event time signal in response to an R-wave sensing threshold crossing by ventricular signal 153 during the non-overlapping portion 167 of post-atrial time interval 162 and post-atrial blanking period 160. The event time signal during non-overlapping portion 167 causes control circuit 80 to accumulate oversensing evidence. As such, an R-wave sensing threshold crossing during post-atrial time interval 162 but outside post-atrial ventricular blanking period may cause both withholding of a scheduled ventricular pacing pulse and detection of oversensing evidence by control circuit 80. Oversensing evidence accumulated during the non-overlapping portion 167 may be used by control circuit 80 to extend post-atrial ventricular blanking period 160 to expire later than event time signals received during the non-overlapping portion 167 and/or increase the ventricular sensitivity setting to avoid sensing events during the non-overlapping portion 167.

Figure 7:
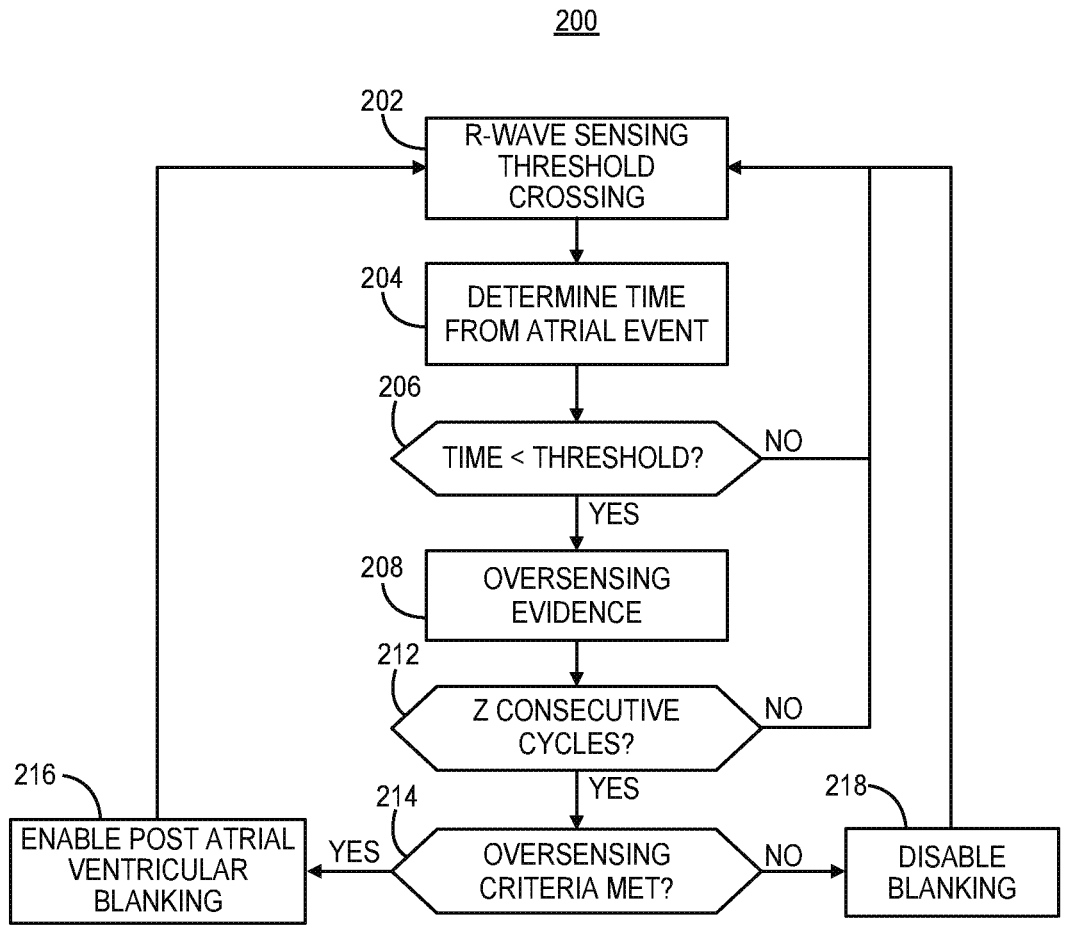
FIG. 7 is a flow chart of one method that may be performed by a medical device for accumulating oversensing evidence and adjusting ventricular sensing control parameters.

FIG. 7 is a flow chart 200 of a method that may be performed by a medical device, such as IMD 14 or pacemaker 100, for accumulating oversensing evidence and adjusting ventricular sensing control parameters according to one example. At block 202, control circuit 80 may determine that an R-wave sensing threshold crossing has occurred. This determination may be made based on an event time signal 186 received from the oversense event detector 180 and/or from an R-wave sensed event signal 178 received from ventricular event detector 176. In some examples, only R-wave sensing threshold crossings that occur during the post-atrial time interval are identified at block 202 for use in detecting oversensing evidence. An R-wave sensing threshold crossing occurring outside the post-atrial time interval at block 202 may be ignored for the purposes of detecting oversensing evidence according to the methods of FIG. 7.

At block 204, control circuit 80 may determine the time interval from a preceding atrial event to the time that the R-wave sensing threshold crossing occurred (or a peak amplitude time) and determine if the determined time interval is less than an oversense event time interval threshold. The oversense event time interval threshold may correspond to the post-atrial time interval, e.g., post-atrial time interval 162 in FIG. 6, during which an R-wave sensing threshold crossing may be caused by an atrial event (sensed or paced) or a cardiac potential signal. If the R-wave sensing threshold crossing occurs later than the oversense event time interval threshold, e.g., outside the post-atrial time interval 162, control circuit 80 returns to block 202 to wait for the next R-wave sensing threshold crossing. An R-wave sensing threshold crossing later than the oversense event time interval threshold from a preceding P-wave sensed event signal or delivered atrial pacing pulse is not counted as evidence for possible oversensing.

In some examples, control circuit 80 may determine that the time from an atrial event (sensed or paced) to an R-wave sensing threshold crossing is less than the oversense event time interval threshold based on receiving an event time signal 186 from oversense event detector 180 (as shown in FIG. 5). Oversense event detector 180 may be enabled to generate an event time signal 186 only during a post-atrial time interval. As such, when control circuit 80 receives an event time signal from oversense event detector 180, the corresponding R-wave sensing threshold crossing is within the oversense event time interval threshold at block 206. In some instances, when post-atrial ventricular blanking is not enabled or when the post-atrial time interval is longer than the post-atrial ventricular blanking period, control circuit 80 may also receive an R-wave sensed event signal from ventricular event detector 176 during the post-atrial time interval. The event time signal 186 from oversense event detector 180, however, is evidence of possible or actual oversensing whether or not an R-wave sensed event signal is produced. If no event time signal is received from oversense event detector 180 but an R-wave sensed event signal is received from ventricular event detector 176 at block 202, control circuit 80 may determine that the R-wave sensing threshold crossing was later than the oversense event time interval threshold and return to block 202.

In some examples, the oversense event time interval threshold applied at block 206 may be different when the preceding atrial event is a sensed P-wave than when the preceding atrial event is an atrial pacing pulse. A longer oversense event time interval threshold may be applied when the preceding atrial event starting the oversense event time interval threshold is a pacing pulse since a delay between the delivered atrial pacing pulse and the evoked atrial depolarization exists. For example, the oversense event time interval threshold or post-atrial time interval may be set to 70 to 100 ms or about 80 ms when the preceding atrial event is a sensed P-wave. The time interval threshold or post-atrial time interval may be set to 100 to 120 ms or about 110 ms when the preceding atrial event is an atrial pacing pulse.

In response to determining that the time from an atrial event to the detected R-wave sensing threshold crossing is less than the oversense event time interval threshold, control circuit 80 detects oversensing evidence at block 208. The detected oversensing evidence may or may not correspond to an actual oversensed event that results in ventricular event detector 176 producing a false R-wave sensed event signal. When the post-atrial ventricular blanking is enabled and the R-wave sensing threshold crossing occurs during the post-atrial ventricular blanking period, the oversensing evidence detected at block 208 is evidence of a possible oversensed event, but oversensing does not actually occur or interfere with ventricular pacing control. The oversensing evidence suggests that oversensing would likely occur or is predicted to occur if post-atrial ventricular blanking is disabled.

At blocks 212 and 214, control circuit 80 may determine if accumulated oversensing evidence meets oversensing criteria. In one example, control circuit 80 may determine if oversensing evidence, e.g., an R-wave sensing threshold by the cardiac electrical signal crossing during the post-atrial time interval, is detected for a threshold number of consecutive ventricular cycles (or following a threshold number of consecutive atrial sensed and/or atrial paced events). For example, control circuit 80 may determine if oversensing evidence was detected for at least three, at least five or other selected number of consecutively detected R-wave sensing threshold crossings that occur within the post-atrial time interval. When occasional or intermittent oversensing evidence is detected based on an isolated R-wave sensing threshold crossing during one post-atrial time interval, the accumulated oversensing evidence may be deemed inadequate to respond to by adjusting ventricular sensing control parameters. Infrequent oversensed atrial events or cardiac potential signals may not interfere with pacing control in a clinically significant manner such that adjustments to the ventricular sensing control parameters, which could reduce true R-wave sensing reliability, may not be justified. In some cases, intermittent or infrequent oversensing evidence detection may be associated with intermittent or non-sustained non-cardiac noise or other signal artifact, which may not warrant ventricular sensing control parameter adjustment.

Control circuit 80 may detect Z consecutive cycles of oversensing evidence when an oversensing evidence counter is increased in response to an R-wave sensing threshold crossing during the post-atrial time interval following Z consecutive atrial events. The threshold number Z of consecutive cycles of detected oversensing evidence may be different when post-atrial ventricular blanking is enabled than when post-atrial ventricular blanking is disabled. When post-atrial ventricular blanking is enabled, evidence of oversensing may be less likely to cause a pause in ventricular pacing. As such, a higher number of consecutively detected oversensing evidence may be required before performing any additional analysis or taking any further corrective action. When post-atrial ventricular blanking is disabled, however, oversensing of atrial events may lead to a pause in ventricular pacing. As such, the number of consecutive cycles during which oversensing evidence is detected may be relatively low, e.g., two consecutive cycles, in order to allow control circuit 80 to take more immediate corrective action by adjusting one or more ventricular sensing control parameters.

When oversensing evidence is detected for at least Z consecutive ventricular cycles at block 212, e.g., during at least Z consecutive post-atrial time intervals, control circuit 80 may apply additional oversensing evidence criteria at block 214. For example, control circuit 80 may additionally require that oversensing evidence is detected for at least X out Y most recent cardiac cycles. To illustrate, control circuit 80 may determine that oversensing criteria are met at block 214 in response to determining that at least six out of twelve R-wave sensing threshold crossings are detected as oversensing evidence and at least three were detected consecutively. As indicated above, these threshold values of X out of Y cardiac cycles with oversensing evidence detections and at least Z consecutive oversensing evidence detections (or other oversensing criteria) may be defined differently when post-atrial ventricular blanking is enabled than when it is disabled. The oversensing criteria applied at block 214 does not necessarily require that actual false R-wave sensed event signals are produced when oversensing evidence is detected. As discussed above, oversensing criteria may be detected and accumulated at block 208, e.g., as a count of R-wave sensing threshold crossings within the post-atrial time interval, even when a post-atrial ventricular blanking period was applied to the ventricular signal by ventricular event detector 176, precluding oversensing of an event signal that may occur during the blanking period.

When oversensing criteria are met at block 214, control circuit 80 may enable post-atrial ventricular blanking at block 216. In some instances, post-atrial ventricular blanking may already be enabled and, if so, remains enabled. In other instances, post-atrial ventricular blanking may not be currently enabled, and accumulated oversensing evidence warrants enabling the post-atrial ventricular blanking, whether or not actual oversensing has occurred, to avoid or minimize the likelihood of oversensing by ventricular event detector 176.

The post-atrial ventricular blanking period may be set to a fixed value or may be adjustable based on determining the time from a P-wave sensed event signal or atrial pacing pulse to the R-wave sensing threshold crossing identified as oversensing evidence. For example, a default maximum post-atrial ventricular blanking period may be enabled, however, if the time interval from the preceding atrial event to the R-wave sensing threshold crossing identified as oversensing evidence is a more than a safety interval less than the default maximum post-atrial ventricular blanking period, the blanking period may be shortened. The blanking period may be shortened by a predetermined decrement. For instance, a 120 ms maximum blanking period may be shortened to 110 or 100 ms, as long as the post-atrial ventricular blanking period is at least longer than an oversensing evidence event time following the atrial event, e.g., later than an oversensing event time signal after an atrial event. In other examples, the post-atrial ventricular blanking period may be decreased from a maximum period to an interval that is a predetermined safety interval (e.g., 10 to 30 ms) or predetermined percentage longer than the time interval from a most recent preceding atrial event to the event detected as oversensing evidence. This time interval may be determined by control circuit 80 at block 204, e.g., in response to an event time signal received from oversense event detector 180 (FIG. 5).

In still other examples, control circuit 80 may determine multiple A-OS (atrial to oversense event) time intervals between multiple pairs of one atrial event and one subsequent R-wave sensing threshold crossing identified as oversensing evidence. When two events, e.g., one associated with an atrial event and one associated with a cardiac potential signal, occur during one post-atrial time interval, the longer A-OS time interval may be determined. Control circuit 80 may determine a maximum A-OS time interval at block 216 in response to oversensing criteria being met. The maximum A-OS time interval may be determined from the detected oversensing evidence that contributed to oversensing criteria being met at block 214. Control circuit 80 may set the post-atrial ventricular blanking period at block 216 based on the maximum A-OS time interval. For example, the post-atrial ventricular blanking period may be set equal to or a predetermined safety interval or percentage greater than the maximum A-OS time interval. The post-atrial ventricular blanking period may therefore be a variable time period and may be limited up to some maximum allowable blanking period, e.g., up to a maximum of 120 or 130 ms.

When post-atrial ventricular blanking is enabled at block 216, two different blanking periods may be applied by ventricular event detector 176. A shorter blanking period may be started in response to receiving a P-wave sensed event signal and a longer blanking period may be started in response to delivery of an atrial pacing pulse. The post-atrial ventricular blanking period set in response to a P-wave sensed event signal may be 80 ms, and the blanking period set in response to an atrial pacing pulse may be 110 ms, as examples, though shorter or longer blanking periods may be selected and may be tailored to a given patient. As described above, each of the post-atrial sensed event ventricular blanking period and the post-atrial paced event ventricular blanking period may be set individually based on A-OS time intervals determined following atrial sensed P-waves and following atrial pacing pulses, respectively.

When oversensing criteria are not met at block 214, control circuit 80 may disable post-atrial ventricular blanking at block 218. If post-atrial ventricular blanking is enabled and being applied by ventricular event detector 176, but accumulated oversensing evidence fails to meet oversensing criteria at block 214, the post-atrial ventricular blanking may be disabled at block 218 with reasonably low risk of false R-wave sensed event signals being produced by ventricular event detector 176. When oversensing is determined to be unlikely, based on oversensing criteria not being met at block 214, disabling post-atrial ventricular blanking enables R-wave sensing during a greater portion of the ventricular cycle, thereby improving R-wave sensing reliability for pacing control and cardiac rhythm detection. For example, being able to sense R-waves during a greater portion of the ventricular cycle may improve detection of fast ventricular rhythms such as ventricular tachycardia or fibrillation. In some instances, post-atrial ventricular blanking may already be disabled when oversensing criteria are determined to be unmet at block 214, in which case post-atrial ventricular blanking remains disabled at block 218.

After either enabling or disabling post-atrial ventricular blanking at one of blocks 216 or 218, control circuit 80 returns to block 202 to wait for the next R-wave sensing threshold crossing. The process of flow chart 200 may be executed periodically or continuously in response to each R-wave sensing threshold crossing. Each time the oversensing criteria are met, post-atrial ventricular blanking is enabled or remains enabled. Each time oversensing criteria are not met, post-atrial ventricular blanking is disabled or remains disabled. The frequency of enabling and disabling post-atrial ventricular blanking is limited by setting the oversensing criteria used at block 214. For example, requiring Z consecutive R-wave sensing threshold crossings to be identified as oversensing evidence and requiring X out Y R-wave sensing threshold crossings to be identified as oversensing evidence before oversensing criteria are met prevents frequent disabling and re-enabling of post-atrial ventricular blanking and requires sufficient evidence of possible oversensing before blanking is enabled. In this way, post-atrial ventricular blanking is not likely to be repeatedly and frequently enabled and disabled, e.g., on alternating heart beats. The Z consecutive R-wave sensing threshold crossings identified as oversensing evidence may be required to be R-wave sensing threshold crossings occurring during Z consecutive post-atrial time intervals, e.g., based on event time signals generated by oversense event detector 180 with or without intervening R-wave sensing threshold crossings occurring outside the post-atrial time intervals and associated with R-wave sensed event signals.

Figure 8:
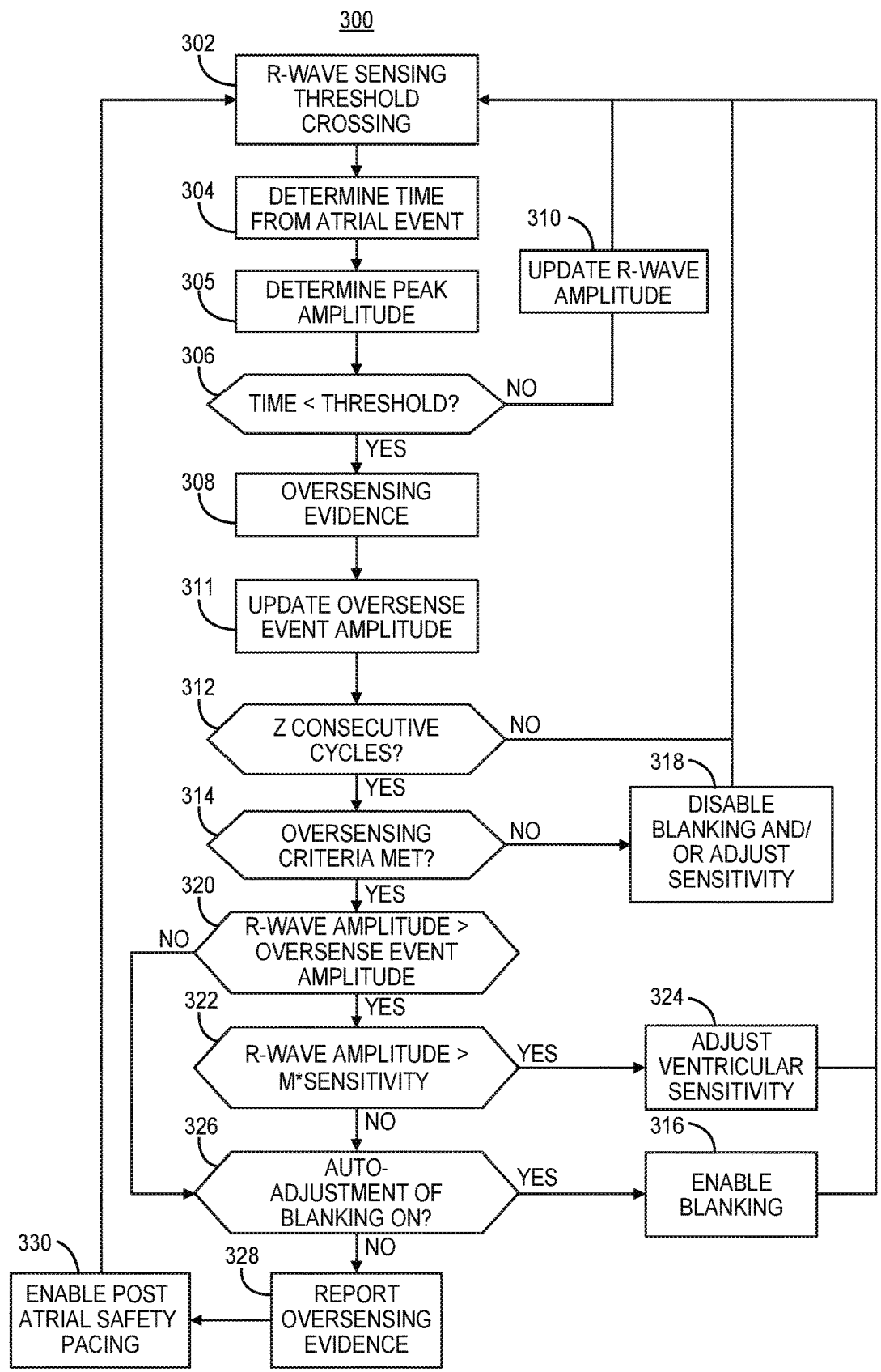
FIG. 8 is a flow chart of a method for accumulating oversensing evidence and adjusting ventricular sensing control parameters based on the accumulated oversensing evidence according to another example.

FIG. 8 is a flow chart 300 of a method for accumulating oversensing evidence and adjusting ventricular sensing control parameters based on the accumulated evidence according to another example. At block 302, control circuit 80 identifies an R-wave sensing threshold crossing as described above in conjunction with FIG. 7. The R-wave sensing threshold crossing may be identified in response to an event time signal from oversense event detector 180. The time from the most recent preceding atrial event, sensed or paced, to the R-wave sensing threshold crossing may be determined at block 304.

At block 305, control circuit 80 may determine the maximum peak amplitude of the ventricular signal following the R-wave sensing threshold crossing. As described above in conjunction with FIG. 5, the peak amplitude may be determined by oversense event detector 180 and an amplitude signal 188 may be passed to control circuit 80. In other examples, control circuit 80 may receive a ventricular EGM signal 185 from ventricular channel 89 and the event time signal 186 from oversense event detector 180. Control circuit 80 may determine the maximum peak amplitude of the ventricular EGM signal 185 following the event time signal 186 but within the post-atrial time interval. A peak time signal 187 may be passed to control circuit 80 for marking the peak time of the event. In various examples disclosed herein, the time of the R-wave sensing threshold crossing or the time of the peak amplitude may be used by control circuit 80 as the event time, e.g., for determining the time interval from the atrial event at block 304. At other times, control circuit 80 may identify the R-wave sensing threshold crossing at block 302 based on an R-wave sensed event signal 178 received from ventricular event detector 176 and determine the maximum peak amplitude of the ventricular EGM signal 185 following the R-wave sensed event signal.

If the determined time interval from the preceding atrial event to the identified R-wave sensing threshold crossing (or peak time) is not less than an oversense event time interval threshold ("no" branch of block 306), e.g., within the post-atrial time interval, oversensing evidence is not detected. The peak amplitude determined at block 305 may be used to update a metric of R-wave amplitude at block 310. For example, a running mean, median, minimum or other metric of sensed R-wave amplitudes may be determined using the peak amplitude determined at block 305, which was not detected as oversensing evidence. The R-wave amplitude metric may be determined based on the most recent 3, 6, 8, 12, 20 or other predetermined number of R-wave sensing threshold crossings that are not detected as oversensing evidence. After updating the R-wave amplitude metric at block 310, control circuit 80 returns to block 302 to wait for the next R-wave sensing threshold crossing.

When oversensing evidence is detected at block 308, e.g., based on the time of the R-wave sensing threshold crossing (or peak time) from a most recent preceding atrial event being within the post-atrial time interval, control circuit 80 may determine an oversense event amplitude metric at block 311. The maximum peak amplitude following the R-wave sensing threshold crossing determined at block 305 may be used to update the oversense event amplitude metric at block 311. The oversense event amplitude metric may be updated to be equal to a mean, median, maximum or other metric determined from a predetermined number of the R-wave sensing threshold crossings recently detected as oversensing evidence. For example, the highest maximum peak amplitude value out of the most recent 3 to 12 peak amplitudes determined for events identified as oversensing evidence may be updated as the oversense event amplitude metric at block 311. It is noted that the oversense event amplitude metric may be determined from signals identified as oversensing evidence which may or may not be actually oversensed as false R-waves or cause an R-wave sensed event signal to be generated by ventricular event detector 176.

At block 312, control circuit 80 determines if at least Z consecutive R-wave sensing threshold crossings are detected as oversensing evidence. If not, control circuit 80 may update oversensing evidence counter(s) for tracking the oversensing evidence at block 312 and return to block 302. For example, a consecutive Z oversensing evidence counter may be reset to zero. The Y value of an X of Y counter may be increased. If oversensing evidence is detected for Z consecutive R-wave sensing threshold crossings as determined at block 312, control circuit 80 determines whether oversensing criteria are met at block 314. As described above, X out of Y consecutive R-wave sensing threshold crossings may be required to be detected as oversensing evidence. If not, control circuit 80 may disable post-atrial ventricular blanking at block 318 (or blanking may remain disabled) and return to block 302.

When oversensing criteria are met at block 314, control circuit 80 may analyze the oversense event amplitude metric and/or the R-wave amplitude metric at block 320. Based on this analysis, control circuit 80 may select an adjustment to ventricular sensing control parameters. For example, control circuit 80 may select between enabling post-atrial ventricular blanking and adjusting ventricular sensitivity to reduce the likelihood of oversensing by the ventricular event detector 176. In order to select adjusting ventricular sensitivity instead of enabling post-atrial ventricular blanking in response to oversense criteria being met, the R-wave amplitude metric may be required to be greater than the oversense event amplitude metric and/or at least some multiple greater than the current ventricular sensitivity setting.

For example, at block 320, the R-wave amplitude metric may be compared to the oversense event amplitude metric. The R-wave amplitude metric may be required to be a predetermined multiple, percentage or fixed difference greater than the oversense event amplitude metric in order to select ventricular sensitivity adjustment instead of enabling post-atrial ventricular blanking. For instance, the R-wave amplitude metric may be required to be at least two times or at least three times the oversense event amplitude metric.

Additionally or alternatively, at block 322 the R-wave amplitude metric may be compared to the current ventricular sensitivity setting that is used for controlling the R-wave sensing threshold. The R-wave amplitude metric may be required to be at least a predetermined multiple, percentage or fixed difference greater than the sensitivity setting, e.g., two times or three times greater than the current ventricular sensitivity setting, in order to select ventricular sensitivity adjustment instead of enabling post-atrial ventricular blanking.

When the R-wave amplitude metric does meet the amplitude criteria relative to the oversense amplitude metric and/or relative to the current ventricular sensitivity setting, control circuit 80 may select to adjust the ventricular sensitivity at block 324. In various examples, one or both requirements represented by blocks 320 and 322 may be required to be met in order to select ventricular sensitivity adjustment at block 324. The ventricular sensitivity may be adjusted by a predetermined increment, e.g., by 0.1 millivolts, 0.2 millivolts, 0.25 millivolts, 0.3 millivolts, 0.5 millivolts or other increment. In other examples, the ventricular sensitivity setting may be adjusted to a setting that is greater than the oversense event amplitude metric by a predetermined amplitude difference, multiple or percentage of the oversense event amplitude metric. The ventricular sensitivity setting may be increased up to a maximum value that is a fraction or percentage of the R-wave amplitude metric, e.g., one-half or one-third of the R-wave amplitude metric.

When the R-wave amplitude metric is not sufficiently greater than the oversense event amplitude metric and/or the ventricular sensitivity setting ("no" branches of blocks 320 and/or 322), or the ventricular sensitivity setting cannot be adjusted to a value that is sufficiently greater than the oversense event amplitude metric and less than the R-wave amplitude metric, control circuit 80 may select to enable post-atrial ventricular blanking instead of adjusting the ventricular sensitivity setting. Control circuit 80 may enable post-atrial ventricular blanking at block 316.

In some examples, a clinician or user may be able to program the medical device to automatically enable and disable post-atrial ventricular blanking. A clinician or user may choose to turn "off" automatic enabling and disabling of the post-atrial ventricular blanking period in some patients, however. For example, a patient with a history of tachyarrhythmia may be at risk for undersensing of ventricular tachyarrhythmia if post-atrial ventricular blanking is enabled. A user may therefore choose to turn off the feature of automatic enabling and disabling of post-atrial ventricular blanking in some patients.

When automatic adjustment of blanking is programmed "on", as determined at block 326, control circuit 80 may automatically enable and disable post-atrial ventricular blanking in response to oversensing criteria being met or not met, respectively. When auto-adjustment of post-atrial ventricular blanking is programmed off by a clinician or other user, post-atrial ventricular blanking is permanently disabled and cannot be automatically enabled by control circuit 80 until a user programs post-atrial ventricular blanking adjustment on.

If automatic blanking period adjusting is programmed on when oversensing criteria are met but the R-wave amplitude metric fails to meet ventricular sensitivity adjustment criteria ("yes" branch of block 326), control circuit 80 enables post-atrial ventricular blanking at block 316. The post-atrial ventricular blanking period may be set to a predetermined maximum blanking period or based on a maximum A-OS time interval determined from an atrial event to an R-wave sensing threshold detected as oversensing evidence. As described above, control circuit 80 may set the post-atrial ventricular blanking period that follows an atrial sensed event to a different, shorter time interval than the post-atrial ventricular blanking period that follows an atrial pacing pulse. Each of these post-atrial sense and post-atrial pace ventricular blanking periods may be based on time intervals measured from respective atrial sense and atrial pace events to respective R-wave sensing threshold crossings detected as oversensing evidence.

When auto-adjustment of post-atrial ventricular blanking is programmed off ("no" branch of block 326, control circuit 80 may withhold adjustment of ventricular sensing control parameters in response to the oversensing criteria being met and the R-wave amplitude metric not meeting criteria required for adjusting the ventricular sensitivity. In this case, control circuit 80 may provide one or more other responses to the oversensing criteria being met. In some examples, control circuit 80 may generate a notification or report of the oversensing evidence at block 328, e.g., to be transmitted to an external device such as device 50 in FIG. 1. The notification or report may be stored in memory 82 until the next interrogation session with external device 50. In other examples, the notification or report may be transmitted without delay to external device 50 to alert the patient or clinician that oversensing may be occurring and may be interfering with appropriate therapy delivery.

A patient or clinician may receive the notification or report from the external device 50. The patient may receive an oversensing notification, for example, and be instructed to seek medical advice or attention to enable his/her clinician to review the oversensing evidence and reprogram ventricular sensing control parameters or other IMD control parameters as needed. In other examples, a clinician may receive the oversensing evidence report through a remote patient monitoring system via external device 50 and send programming instructions to external device 50 for reprogramming IMD control parameters, which may include ventricular sensing control parameters, or at least enabling automatic post-atrial ventricular blanking adjustment.

Additionally or alternatively, control circuit 80 may adjust ventricular sensing control parameters by enabling post-atrial safety pacing at block 330 when oversensing criteria are met and automatic enabling of the post-atrial blanking period is turned "off." In some examples, automatic enabling of post-atrial safety pacing may be a programmable feature. For instance, a clinician may be able to program automatic enabling and disabling of post-atrial safety pacing by control circuit 80 on or off. When enabling of post-atrial safety pacing is programmed on, a post-atrial safety pacing interval may be enabled by control circuit 80 at block 330. The post-atrial safety pace interval is a sensing window during which any R-wave sensed event signal produced by ventricular event detector 176 is plausibly an oversensed atrial event or oversensed cardiac potential signal. Therapy delivery circuit 84 may be configured to generate a ventricular safety pacing pulse in response to an R-wave sensed event signal that is received within the post-atrial safety pace interval after an atrial sensed or paced event. The ventricular safety pacing pulse may be generated and delivered at the expiration of the post-atrial safety pace interval. The post-atrial safety pace interval may be a time interval that is at least encompassed by the ventricular physiological refractory period so that if the R-wave sensing threshold crossing during the post-atrial safety pace interval is a true R-wave, the ventricular safety pace will fail to capture the ventricles due to the refractoriness of the His-Purkinje system and/or ventricular myocardial tissue. If the R-wave sensing threshold crossing during the post-atrial safety pace interval is an atrial event falsely sensed as an R-wave, the ventricular safety pace is likely to capture and produce a ventricular beat since the cardiac tissue is not in a refractory state.

The post-atrial safety pace interval may be set following both atrial sensed events (P-wave sensed event signals) and atrial pacing pulses. After an atrial event, sensed or paced, control circuit 80 may start the safety pace interval, which may be set to a shorter interval following an atrial sensed event than following an atrial pacing pulse in some examples. In some examples, the safety pace interval may be equal to the post-atrial time interval or the post-atrial ventricular blanking period. Additionally, control circuit 80 may start an AV pacing interval (for delivering an atrial synchronized ventricular pacing pulse) in response to the atrial event. Therapy delivery circuit 84 generates and delivers a ventricular pacing pulse at the expiration of the safety pace interval in response to an R-wave sensed event signal produced by ventricular event detector 176 during the safety pace interval. Therapy delivery circuit 84 withholds the safety pace when no R-wave sensed event signal is produced during the safety pace interval and delivers the scheduled ventricular pacing pulse at the expiration of the AV pacing interval. The ventricular pacing pulse scheduled at the AV pacing interval may be withheld when an R-wave sensed event signal is generated by ventricular event detector 176 after the safety pace interval but before the AV pacing interval expires. During single chamber ventricular pacing, the ventricular pacing pulse may be scheduled at a lower rate VV pacing interval instead of the AV pacing interval and be delivered at the expiration of the lower rate VV pacing interval in the absence of an R-wave sensed event signal during the safety pace interval and the VV pacing interval.

Since control circuit 80 is configured to inhibit a ventricular pacing pulse scheduled at an AV interval or VV interval in response to an R-wave sensed event signal, enabling the safety pace interval following atrial events avoids a pause in the ventricular rhythm when the R-wave sensed event signal is false. Adjustment of the ventricular sensing control parameters by setting a safety pace interval, allows control circuit 80 to identify a probable oversensed event when post-atrial ventricular blanking is disabled and avoid a pause in the ventricular rhythm due to oversensing.

While not shown explicitly in FIG. 8, post-atrial safety pacing, if enabled, may be disabled at block 316 when post-atrial ventricular blanking is enabled. A user or clinician may program auto-adjustment of post-atrial ventricular blanking to "on" in response to receiving an oversensing evidence notification or report (block 328). The next time the oversensing criteria are met at block 314, and the R-wave amplitude metric does not meet criteria required for adjustment of the ventricular sensitivity setting, control circuit 80 may enable post-atrial ventricular blanking at block 316 and disable the post-atrial safety pacing. In some examples, post-atrial safety pacing may be disabled following only atrial sensed events (P-wave sensed event signals), but the post-atrial safety pacing may remain enabled following atrial paced events, whether blanking is enabled or not, since atrial pacing artifact may be more likely to be oversensed by the ventricular channel 89 than atrial P-waves.

Furthermore, it is recognized that any ventricular sensing control parameter adjustments made in response to oversensing criteria being met may be reversed when oversensing criteria are no longer met. For example, when oversensing criteria are not met at block 314 and post-atrial ventricular blanking is disabled at block 318, the post-atrial safety pacing that had been previously enabled at block 330 may be disabled in response to oversensing criteria not being met. The post-atrial safety pacing may be disabled, in conjunction with disabling post-atrial ventricular blanking at block 318. The post-atrial safety pacing may be disabled at least following atrial sensed events. The post-atrial safety pacing may remain enabled following atrial pacing pulses when post-atrial blanking is disabled at block 318, at least in some examples, since oversensing of atrial pacing artifact may occur when blanking is disabled.

When the ventricular sensitivity setting has been increased at block 324 in response to oversensing criteria being met and the R-wave amplitude metric meeting sensitivity adjustment criteria, the ventricular sensitivity setting may be decreased to a lower setting at block 318 in response to oversensing criteria no longer being met at block 314. In some cases, the ventricular sensitivity setting (in millivolts) may be decreased at block 318 in addition to disabling post-atrial ventricular blanking. In order to decrease the ventricular sensitivity setting in conjunction with disabling blanking at block 318, the R-wave amplitude metric may be required to be a predetermined multiple greater than the decreased sensitivity setting and/or a predetermined multiple greater than the oversense event amplitude metric. The oversense event amplitude metric may be required to be less than the decreased sensitivity setting by at least a safety margin in some examples.

Criteria may be applied to the relative differences or ratios of the R-wave amplitude metric and the oversense event amplitude metric, the R-wave amplitude metric and the pending, decreased ventricular sensitivity setting, and/or the oversense event amplitude metric and the pending, decreased ventricular sensitivity setting before adjusting the ventricular sensitivity setting to a decreased setting. To illustrate, the R-wave amplitude metric may be verified to be at least two to three times greater than the pending decreased sensitivity setting, and/or the oversense event amplitude metric may be required to be less than the decreased sensitivity setting. If criteria for decreasing the sensitivity setting are not satisfied, the sensitivity setting may remain at the previously increased sensitivity setting even when oversensing criteria are no longer met at block 314.

Figure 9:
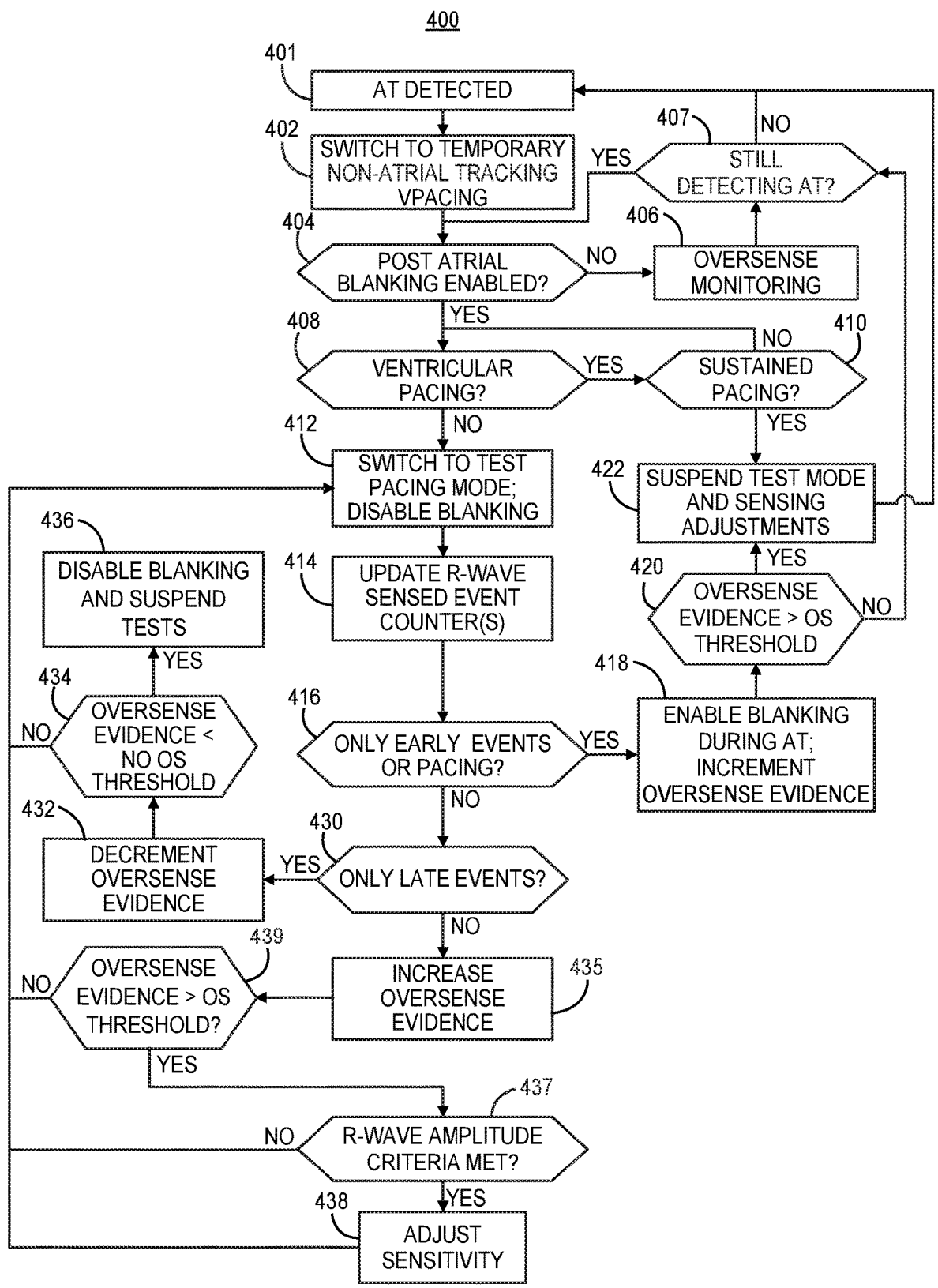
FIG. 9 is a flow chart of a method for controlling ventricular sensing control parameters by an IMD based on oversensing evidence in the presence of an atrial tachyarrhythmia (AT) according to one example.

FIG. 9 is a flow chart 400 of a method for controlling ventricular sensing control parameters by an IMD based on oversensing evidence in the presence of an atrial tachyarrhythmia (AT) according to one example. Atrial tachyarrhythmia, which may include different forms of fast atrial rhythms such as atrial flutter, atrial tachycardia and atrial fibrillation, may be detected by control circuit 80 at block 401 based on an analysis of the digital EGM signals generated by sensing circuit 86 and passed to control circuit 80 and/or analysis of PP intervals between consecutive P-wave sensed event signals, RR intervals between consecutive R-wave sensed event signals, RP and/or PR intervals between consecutive P-wave sensed event signals and R-wave sensed event signals. Control circuit 80 may switch from an atrial tracking ventricular pacing mode to a temporary non-tracking ventricular pacing mode (block 402) in response to detecting AT to promote a regular ventricular rate during AT that does not track the fast atrial rate. Ventricular pacing pulses may be delivered at a programmed ventricular lower rate interval in the absence of an R-wave sensed event signal.

During AT, atrial signals may be relatively lower in amplitude than normal sinus P-wave signals such that atrial event oversensing by the ventricular event detector 176 may be less likely to occur during AT than during a normal sinus atrial rhythm or a paced atrial rhythm. However, atrial event oversensing (or oversensing of cardiac potential signals) could still occur during AT in some instances and since the atrial depolarizations are occurring at a fast and sometimes irregular rate depending on the type of AT, atrial events may be oversensed frequently and/or at irregular intervals by the ventricular event detector 176, causing ventricular pacing pulses to be inhibited. If post-atrial ventricular blanking is enabled at the time that AT is detected, blanking of true R-waves (which may be occurring at an irregular rate) could occur potentially resulting in competitive ventricular pacing. In this situation, ventricular pacing pulses may be delivered at the expiration of a VV lower rate interval even though an intrinsic ventricular depolarization occurred during a post-atrial ventricular blanking period. Accordingly, techniques for accumulating oversensing evidence during AT, particularly when post-atrial ventricular blanking is enabled, may be modified from the techniques described in conjunction with FIGS. 7 and 8, which may be used during normal sinus or paced atrial rhythms.

When post-atrial blanking is not enabled during the detected AT, "no" branch of block 404, control circuit 80 may continue to accumulate oversensing evidence and adjust ventricular sensing control parameters according to the techniques of FIG. 7 or 8. The risk of competitive ventricular pacing is lower when post-atrial ventricular blanking is disabled since ventricular event detector 176 is not blinded to true R-waves that occur early after atrial events. As such, special monitoring for oversensing evidence may not be required during AT as long as blanking is disabled. However, if post-atrial ventricular blanking is enabled at the time AT is detected, or becomes enabled during a sustained AT due to oversensing criteria being met at block 406 according to the techniques of FIG. 7 or FIG. 8, control circuit 80 may modify the techniques for monitoring for oversensing evidence during AT according to the flow chart of FIG. 9. Since atrial event oversensing may occur at fast and/or irregular time intervals during AT, atrial event oversensing may occur at various times in the ventricular cycle and even multiple times during a ventricular cycle. Oversensing evidence during AT may be more challenging to detect than during a slower, sinus atrial rhythm or paced atrial rhythm. Yet because competitive ventricular pacing could occur when blanking is enabled, techniques of FIG. 9 may be executed to detect evidence of oversensing and respond appropriately to minimize the likelihood of competitive ventricular pacing as well as pauses in the ventricular rhythm due to oversensing.

If post-atrial ventricular blanking is enabled ("yes" branch of block 404), control circuit 80 may determine if the ventricular rhythm is a predominately a paced rhythm at the programmed ventricular rate at block 408. When no R-waves are being sensed (or rarely being sensed), the absence of R-wave sensed event signals is an indication that the patient is pacemaker dependent. If no or few R-wave sensed event signals are occurring outside the post-atrial ventricular blanking period, oversensing is improbable. Therefore, searching for sensed events that may be oversensed events is unnecessary as long as the predominately paced ventricular rhythm is sustained. The patient is receiving appropriate ventricular rate support and the likelihood of competitive ventricular pacing is small if there is no evidence of R-wave sensing.

Predominate ventricular pacing may be identified at block 408 based on a predetermined number of consecutive pacing pulses or the ratio of R-wave sensed event signals to delivered ventricular pacing pulses being very small, e.g., 1:5, 1:6, 1:8, 1:10, 1:20 or even lower. The threshold for detecting predominate ventricular pacing may be modulated based on pacing history. For example, if the patient has been highly pacemaker dependent, e.g., with a high percentage of ventricular pacing, predominate pacing is likely to be true so a lower predominate pacing threshold may be used.

When predominate pacing is detected at block 408, control circuit 80 may determine if the predominate pacing has been sustained for a threshold time interval (or number of pacing cycles). Sustained predominate pacing may be detected when pacing is detected for at least one minute in one example. When sustained, predominate ventricular pacing is detected, control circuit 80 may suspend any further monitoring for oversensing evidence at block 422 as long as AT is being detected. Ventricular rate support is properly being provided and risk of ventricular competitive pacing is acceptably low. Post-ventricular atrial blanking can be maintained. In some examples, control circuit 80 may suspend operations for collecting oversensing evidence during the detected AT episode at block 422. Control circuit 80 may return to block 401 and repeat the process of flow chart 400 the next time an AT episode is detected. In other examples, control circuit 80 may temporarily suspend operations for collecting oversensing evidence at block 422 for a predetermined time interval, e.g., one minute, two minutes, five minutes or other time interval, which may be an increasing time interval, then return to block 407 to determine if AT is still being detected with post-atrial ventricular blanking enabled and predominate, sustained ventricular pacing.

If sustained ventricular pacing is not detected, control circuit 80 may wait for predominate ventricular pacing to become sustained at block 410 (by returning to block 408). However, if control circuit 80 no longer detects predominate ventricular pacing at block 408 (and the AT episode is still being detected), control circuit 80 may execute modified oversensing monitoring techniques beginning at block 412. At block 412, control circuit 80 switches to a test mode for monitoring for oversensing evidence. The test mode may be applied for at least one ventricular cycle. For example, when the AT is detected, control circuit 80 may switch to operating in a temporary non-atrial tracking pacing mode (block 402) and post-atrial ventricular blanking may be enabled (block 404). In response to not detecting predominate ventricular pacing in the temporary non-atrial tracking ventricular pacing mode, control circuit 80 may be configured to switch from the temporary non-atrial tracking ventricular pacing mode to a test mode of atrial tracking ventricular pacing at block 412 with post-atrial ventricular blanking disabled. In some examples, the pacing mode is switched to an atrial tracking mode with post-atrial ventricular blanking disabled for only a single ventricular cycle and then returns to the temporary non-atrial tracking ventricular pacing mode with blanking re-enabled. In other examples, control circuit 80 may switch to the test mode of atrial tracking ventricular pacing mode with post-atrial ventricular blanking disabled for up to three or another limited number of ventricular cycles.

At block 414, control circuit 80 updates an R-wave sensed event counter for each R-wave sensed event signal received from ventricular event detector 176 during the atrial tracking pacing mode with post-atrial ventricular blanking disabled. One R-wave sensed event counter may be used to count the number of R-wave sensed event signals that occur within a post-atrial time interval of an atrial event. A second R-wave sensed event counter may be used to count the number of R-wave sensed event signals that occur after the post-atrial time interval. For example, an early sensed event counter may be increased in response to an event time signal produced by oversense event detector 180 coincidentally with an R-wave sensed event signal 178 produced by ventricular event detector 176. A different, late sensed event counter may be increased in response to an R-wave sensed event signal 178 that is produced by ventricular event detector 176 when no corresponding event time signal 186 is produced by oversense event detector 180 (which may be disabled outside the post-atrial time interval). The R-wave sensed event counters are updated according to the timing of the R-wave sensed event signals relative to a post-atrial time interval each time the atrial tracking ventricular pacing mode is in effect.

At block 416, based on the counter values updated at block 414, control circuit 80 determines if R-wave sensed events are occurring during the test mode only during the post-atrial time interval or if a ventricular pacing pulse (no R-wave sensed event signal) occurred. If only ventricular pacing occurred during the test pacing mode, both counter values will be zero. If R-wave sensed event signals occurred only during the post-atrial time interval, the corresponding early event counter will be a non-zero value while the late event counter corresponding to R-wave sensed event signals outside the post-atrial time interval will be zero. If only early, post-atrial events are sensed and/or ventricular pacing was delivered during the test mode, control circuit 80 re-enables post-atrial ventricular blanking upon switching back to the temporary non-atrial tracking ventricular pacing mode (from the test pacing mode) at block 418. Early events are evidence of potential oversensing, warranting post-atrial ventricular blanking.

As such, an oversense evidence counter may be incremented at block 418 in response to determining that R-wave sensed event signals produced during the test pacing mode were early events, occurring during a post-atrial time interval. The oversense evidence counter may be compared to a threshold value at block 420. The oversense threshold may require at least six detections of oversensing evidence out of nine test pacing mode cycles as an example (or other X out of Y criteria). When the oversense evidence threshold is exceeded, the probability of oversensing during the detected AT is high. The test mode and oversense evidence monitoring during AT may be suspended at block 422, leaving post-atrial ventricular blanking enabled. The testing mode during AT may be suspended when the oversensing evidence counter reaches a threshold value of at least 3, 5, 8, 12 or other predetermined number of test mode ventricular cycles determined to be oversensing evidence, which may or may not be required to be consecutive. The operations for collecting oversense evidence during the AT episode, such as switching to the test mode of atrial-tracking ventricular pacing with post-atrial blanking disabled and updating R-wave sensed event counters, may be suspended at block 422 for the remainder of the currently detected AT episode. Control circuit 80 may return to block 401 to wait for the next AT episode detection. In other examples, control circuit 80 may suspend the test mode temporarily at block 422 for a predetermined time interval then return to block 407 to resume accumulating oversensing evidence according to the modified techniques of FIG. 9 if AT is still being detected.

When the oversense evidence counter is not greater than the threshold at block 420, control circuit 80 may return to block 407. As long as AT is still being detected, ventricular blanking is still enabled, and ventricular pacing is not predominate during the temporary non-atrial tracking pacing mode, control circuit 80 may continue to accumulate oversensing evidence by briefly switching to a test mode at block 412. The early and late R-wave sensed event counters may hold their respective current values and continue to be incremented based on the timing of R-wave sensed event signals during the test mode. The R-wave sensed event counters may be cleared (reset to zero) when control circuit 80 suspends switching to the test mode at block 422 or when AT is no longer being detected.

If the late event counter corresponding to R-waves sensed outside the post-atrial time interval is non-zero and the early sensed event counter corresponding to R-waves sensed during the post-atrial time interval is zero, control circuit 80 determines that only "late" R-waves are sensed that do not occur during the post-atrial time interval at block 430. In this case, control circuit 80 may decrement the oversense evidence counter at block 432. No R-waves are being sensed during the post-atrial time interval when blanking is disabled so there is no evidence of possible oversensing.

If the oversense evidence counter value becomes less than a "no oversensing" threshold value at block 434, e.g., less than 2 after a predetermined number of, e.g., 12, test mode ventricular cycles, control circuit 80 may disable post-atrial ventricular blanking at block 436. Switching to the test mode may also be suspended at block 436 since post-atrial blanking is no longer enabled. Oversense evidence monitoring may be terminated until the AT episode is no longer detected. In some examples, oversense evidence monitoring may continue during the AT episode (at block 406) when post-atrial blanking is disabled according to the techniques described in conjunction with FIG. 7 or 8.

When the oversense evidence counter value is not less than the "no oversensing" threshold value at block 434, control circuit 80 continues to intermittently switch to the test mode at block 412 ("no" branch of block 434). Control circuit 80 may switch to the test pacing mode for one ventricular cycle every fifth cycle, every tenth cycle or other selected frequency to continue to accumulate oversensing evidence (or lack thereof).

In some cases, there may be a mix of early and late R-wave sensed events during the test mode. When both of the early and late R-wave sensed event counters have non-zero values, control circuit 80 advances from block 430 ("no" branch) to block 435. A mix of both early and late R-wave sensed events may indicate evidence of oversensing of the fast and/or irregular atrial rate. In response to detecting a combination of both early (during a post-atrial time interval) and late (after a post-atrial time interval) R-wave sensed events, the oversense evidence counter may be increased at block 435.

Control circuit 80 may determine if the oversense evidence meets oversense evidence criteria at block 439 in response to increasing the oversense evidence at block 435. Oversensing evidence criteria applied to accumulated oversense evidence in the process of flow chart 400 or any of the other flow charts presented herein may include a fixed or an adjustable threshold. An adjustable oversense evidence threshold may be set based on a ratio of the post-atrial time interval to an atrial event interval. Atrial event intervals may be PP intervals determined between consecutive P-wave sensed event signals produced by the atrial channel of sensing circuit 86. In other instances, atrial event intervals may start and/or end with an atrial pacing pulse. In the case of flow chart 400, at block 439, control circuit 80 may determine an atrial event interval of the detected AT interval from PP intervals. During AT, R-waves may occur randomly during any portion of the AT interval, resulting in a mix of both early and late R-wave sensed events ("no" branch of block 430). If the post-atrial time interval is one-third of the total AT interval, for example, true R-waves are expected to occur one-third of the time during the post-atrial time interval and two-thirds of the time after the post-atrial time interval. As such, control circuit 80 may set an oversense evidence threshold at block 439 as a ratio of the post-atrial time interval to the detected AT interval, e.g., one-third in the illustrative example. If more than one-third of the R-wave sensed event signals are early, during the post-atrial time interval, at least some of these early R-wave sensed event signals may be evidence of oversensing. Accordingly, the ratio of the early event counter value to the late event counter value may be compared to an oversense evidence threshold ratio at block 439 that is set based on the ratio of the post-atrial time interval to the AT interval (which may be variable). As the AT interval changes, within or between detected AT episodes, the oversense evidence threshold ratio applied at block 439 may be adjusted.

When this oversense threshold ratio is not exceeded at block 439, control circuit 80 may return to block 412 to repeat the test pacing mode for additional ventricular cycles for monitoring for oversensing during the detected AT episode. While not shown explicitly in FIG. 9, it is to be understood that when the AT episode is no longer being detected, control circuit 80 may suspend the test mode and return to block 401 to wait for the next AT episode detection.

When the oversense evidence threshold ratio (or another fixed oversense evidence threshold) is exceeded at block 439, control circuit 80 may attempt to adjust the ventricular sensitivity to reduce or eliminate the oversensing risk at block 438. At block 437, control circuit 80 may determine if R-wave amplitude criteria. Control circuit 80 may compare an amplitude metric of early events sensed during the post-atrial time interval to an amplitude metric of late events sensed outside the post-atrial time interval or to a previously stored R-wave amplitude metric. As described above in conjunction with FIG. 8, if the R-wave amplitude metric is at least a predetermined multiple, e.g., at least twice, the programmed ventricular sensitivity setting, control circuit 80 may increase the ventricular sensitivity setting at block 438 to reduce the likelihood of oversensing. In some examples, the R-wave amplitude metric may be required to be a predetermined multiple greater than the oversensed event amplitude metric determined from early events and/or a predetermined multiple greater than the ventricular sensitivity setting. Control circuit 80 may increase the ventricular sensitivity setting at block 438 and return to block 412. When the R-wave amplitude criteria are unmet at block 437, control circuit 80 may return to block 412, without adjusting the ventricular sensitivity, to continue switching to the test mode at a predetermined frequency for accumulating oversensing evidence and adjust ventricular sensing control parameters as needed until the AT is no longer detected or the oversense evidence counter is either less than a "no oversense" threshold (block 434) or greater than an oversense threshold at block 420 and testing is suspended (block 436 or block 422, respectively).

The techniques of flow chart 400 may be utilized during a detected AT episode to accumulate oversensing evidence when the atrial rate is fast and/or irregular. When AT is no longer being detected, control circuit 80 may switch back to accumulating oversensing evidence according to the techniques of FIG. 7 or 8. Using the techniques disclosed herein, a medical device is capable of detecting and accumulating evidence of oversensing, even when events are not actually being oversensed or such oversensed events are being ignored and not interfering with ventricular pacing control.

These techniques improve the reliability of ventricular sensing and pacing performance of the medical device performing the techniques, particularly when one or both ventricular sensing electrodes are positioned in close proximity to or even in an atrial chamber. This situation may arise when ventricular pacing is being delivered to the His-Purkinje system as depicted in FIGS. 1-3. Accumulation of oversensing evidence that includes evidence of actual or potential oversensing of atrial events and/or cardiac potential signals is useful in a device that has or is coupled to ventricular sensing electrode(s) that are in close proximity to or in an atrial chamber. When ventricular pacing leads or electrodes are positioned relatively lower in or along the ventricles, e.g., for pacing the ventricular myocardium at the ventricular apex, one or both ventricular sensing electrodes are relatively far from the atrial chambers and His bundle and bundle branches such that oversensing of atrial events and cardiac potential signals, is less likely or improbable. Subsequently, interference of oversensed atrial events or oversensed cardiac potential signals with ventricular pacing control is unlikely in such systems. Nonetheless, the techniques disclosed herein may be implemented in any medical device configured for ventricular sensing when oversensing could interfere with appropriate device operations, such as controlling ventricular pacing and detecting ventricular arrhythmia and delivering ventricular arrhythmia therapies.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of circuits or components associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device, comprising:
   a sensing circuit configured to:
   sense a ventricular electrical signal;
   set an R-wave sensing threshold;
   receive an atrial event signal;
   set a post-atrial time interval in response to the atrial event signal; and
   generate an event time signal in response to the ventricular electrical signal being equal to or greater than the R-wave sensing threshold during the post-atrial time interval; and
   a control circuit configured to:
   determine a count of event time signals generated by the sensing circuit; and
   adjust a ventricular sensing control parameter based on the count of event time signals.

2. The medical device of claim 1, wherein:
   the control circuit is configured to adjust the ventricular sensing control parameter by enabling a post-atrial ventricular blanking period.

3. The medical device of claim 2, wherein:
   the sensing circuit is configured to:
   set the post-atrial time interval and the post-atrial ventricular blanking period in response to receiving a next atrial event signal, the post-atrial time interval and the post-atrial ventricular blanking period at least partially overlapping;
   generate a next event time signal without generating an R-wave sensed event signal in response to the ventricular electrical signal being equal to or greater than the R-wave sensing threshold during an overlapping portion of the post-atrial ventricular blanking period and the post-atrial time interval; and
   the control circuit is configured to increase the count of event time intervals in response to the next event time signal.

4. The medical device of claim 1, wherein the control circuit is configured to:
   determine a time interval from the atrial event signal to the event time signal;
   adjust the ventricular sensing control parameter by adjusting an ending time of a post-atrial ventricular blanking period based on the determined time interval.

5. The medical device of claim 1, wherein the control circuit is configured to adjust the ventricular sensing control parameter by adjusting a ventricular sensitivity setting used to set the R-wave sensing threshold.

6. The medical device of claim 5, wherein the control circuit is configured to:
   determine at least one amplitude metric from the ventricular electrical signal; and
   adjust the ventricular sensitivity setting based on the at least one amplitude metric.

7. The medical device of claim 6, wherein:
   the sensing circuit is configured to:
   generate an R-wave sensed event signal in response to the ventricular electrical signal crossing the R-wave sensing threshold;
   determine from the ventricular electrical signal a peak amplitude associated with the R-wave sensed event signal;

the control circuit is configured to:
  determine the at least one amplitude metric based at least on the peak amplitude; and
  adjust the ventricular sensitivity setting based on the R-wave amplitude metric.

8. The medical device of claim 7, wherein:
the sensing circuit is configured to determine, from the ventricular electrical signal, an oversense event amplitude associated with the event time signal;
the control circuit is configured to:
  determine the at least one amplitude metric by determining an oversense event amplitude metric based at least on the oversense event amplitude; and
  adjust the ventricular sensitivity setting based on a comparison of the R-wave amplitude metric to at least one of the oversense event amplitude and the ventricular sensitivity setting.

9. The medical device of claim 1, wherein the control circuit is configured to:
  adjust the count of the event time signals in response to not receiving an event time signal from the sensing circuit during a next post-atrial time interval;
  adjust the ventricular sensing control parameter by disabling a post-atrial ventricular blanking period based on the adjusted count of the event time signals.

10. The medical device of claim 1, wherein:
the sensing circuit is further configured to:
  generate an R-wave sensed event signal in response to the ventricular electrical signal crossing the R-wave sensing threshold; and
  sense an atrial electrical signal;
the control circuit is configured to:
  detect atrial tachyarrhythmia from the atrial electrical signal;
  determine that the R-wave sensed event signal is generated by the sensing circuit during a post-atrial time interval;
  increase a count of oversensing evidence in response to the R-wave sensed event signal being generated during the post-atrial time interval; and
  enable a post-atrial ventricular blanking period in response to the increased count of oversensing evidence.

11. The medical device of claim 10, wherein the control circuit is configured to:
  determine an atrial event interval between two consecutive atrial event signals;
  set oversensing evidence criteria based on a ratio of the post-atrial time interval to the atrial event interval;
  compare the count of oversensing evidence to the oversensing criteria; and
  enable the post-atrial ventricular blanking period in response to the increased count of oversensing evidence meeting the oversensing evidence criteria.

12. The medical device of claim 1, wherein:
the sensing circuit is further configured to:
  generate an R-wave sensed event signal in response to the ventricular electrical signal crossing the R-wave sensing threshold; and
  sense an atrial electrical signal;
the control circuit is configured to:
  detect atrial tachyarrhythmia from the atrial electrical signal;
  temporarily disable a post-atrial ventricular blanking period in response to detecting the atrial tachyarrhythmia;
  determine that an R-wave sensed event signal is generated by the sensing circuit outside the post-atrial time interval when the post-atrial ventricular blanking period is temporarily disabled; and
  disable the post-atrial ventricular blanking period during the detected atrial tachyarrhythmia in response to at least the R-wave sensed event signal being generated outside the post-atrial time interval when the post-atrial ventricular blanking period is disabled.

13. The medical device of claim 1, further comprising:
a therapy delivery circuit configured to generate atrial pacing pulses;
wherein the sensing circuit is further configured to:
  sense an atrial electrical signal; and
  generate a P-wave sensed event signal in response to the atrial electrical signal crossing a P-wave sensing threshold,
  receive the atrial event signal associated with one of an atrial pacing pulse generated by the therapy delivery circuit or a P-wave sensed event signal generated by the sensing circuit;
  set the post-atrial time interval to a first time duration in response to receiving the atrial event signal associated with a P-wave sensed event signal; and
  set the post-atrial time interval to a second time duration greater than the first time duration in response to receiving the atrial event signal associated with an atrial pacing pulse.

14. The medical device of claim 1, wherein:
the control circuit is configured to adjust the ventricular sensing control parameter by setting a safety pace interval in response to receiving an atrial event signal;
the sensing circuit is configured to generate an R-wave sensed event signal during the safety pace interval in response to the ventricular electrical signal crossing the R-wave sensing threshold during the safety pace interval;
the medical device further comprising a therapy delivery circuit configured to generate a ventricular pacing pulse upon expiration of the safety pace interval in response to the R-wave sensed event signal being generated during the safety pace interval.

15. The medical device of claim 1, wherein the sensing circuit is configured to:
  set a post-atrial ventricular blanking period in response to the atrial event signal; and
  generate an R-wave sensed event signal in response to the ventricular electrical signal crossing the R-wave sensing threshold during the post-atrial time interval and outside the post-atrial ventricular blanking period.

16. The device of claim 1, wherein the control circuit is further configured to:
  compare the count of event time signals to first oversensing criteria when a post-atrial ventricular blanking period is enabled;
  compare the count of event time signals to second oversensing criteria different than the first oversensing criteria when the post-atrial ventricular blanking period is disabled; and
  adjust the ventricular sensing control parameter in response to the count of event time signals meeting one of the first oversensing criteria or the second oversensing criteria.

17. A method, comprising:
sensing a ventricular electrical signal;
setting an R-wave sensing threshold;
receiving an atrial event signal;
setting a post-atrial time interval in response to receiving the atrial event signal;
generating an event time signal in response to the ventricular electrical signal being equal to or greater than the R-wave sensing threshold during the post-atrial time interval;
determining a count of event time signals in response to the generated event time signal; and
adjusting a ventricular sensing control parameter based on the count of event time signals.

18. The method of claim 17, comprising:
adjusting the ventricular sensing control parameter by enabling a post-atrial ventricular blanking period.

19. The method of claim 18, comprising:
setting the post-atrial time interval and the post-atrial ventricular blanking period in response to receiving a next atrial event signal, the post-atrial time interval and the post-atrial ventricular blanking period at least partially overlapping;
generating a next event time signal without generating an R-wave sensed event signal in response to the ventricular electrical signal being equal to or greater than the R-wave sensing threshold during an overlapping portion of the post-atrial ventricular blanking period and the post-atrial time interval; and
increasing the count of event time intervals in response to the next event time signal.

20. The method of claim 17, further comprising:
determining a time interval from the atrial event signal to the event time signal;
adjust the ventricular sensing control parameter by adjusting an ending time of a post-atrial ventricular blanking period based on the determined time interval.

21. The method of claim 17, wherein adjusting the ventricular sensing control parameter comprises adjusting a ventricular sensitivity setting used to set the R-wave sensing threshold.

22. The method of claim 21, comprising:
determining at least one amplitude metric from the ventricular electrical signal; and
adjusting the ventricular sensitivity setting based on the at least one amplitude metric.

23. The method of claim 22, comprising:
generating an R-wave sensed event signal in response to the ventricular electrical signal crossing the R-wave sensing threshold;
determining, from the ventricular electrical signal, a peak amplitude associated with the R-wave sensed event signal;
determining the at least one amplitude metric based at least on the peak amplitude; and
adjust the ventricular sensitivity setting based on the R-wave amplitude metric.

24. The method of claim 23, comprising:
determining, from the ventricular electrical signal, an oversense event amplitude associated with the event time signal;
determining the at least one amplitude metric by determining an oversense event amplitude metric based at least on the oversense event amplitude; and
adjusting the ventricular sensitivity setting based on a comparison of the R-wave amplitude metric to at least one of the oversense event amplitude and the ventricular sensitivity setting.

25. The method of claim 17, comprising:
adjusting the count of the event time signals in response to not receiving an event time signal from the sensing circuit during a next post-atrial time interval;
adjusting the ventricular sensing control parameter by disabling a post-atrial ventricular blanking period based on the adjusted count of the event time signals.

26. The method of claim 17, further comprising:
generating an R-wave sensed event signal in response to the ventricular electrical signal crossing the R-wave sensing threshold;
sensing an atrial electrical signal;
detecting atrial tachyarrhythmia from the atrial electrical signal;
determining that the R-wave sensed event signal is generated by the sensing circuit during a post-atrial time interval;
increasing a count of oversensing evidence in response to the R-wave sensed event signal being generated during the post-atrial time interval; and
enable a post-atrial ventricular blanking period in response to the increased count of oversensing evidence.

27. The method of claim 26, further comprising:
determining an atrial event interval between two consecutive atrial event signals;
set oversensing evidence criteria based on a ratio of the post-atrial time interval to the atrial event interval;
comparing the count of oversensing evidence to the oversensing criteria; and
enabling a post-atrial ventricular blanking period in response to the increased count of oversensing evidence meeting the oversensing evidence criteria.

28. The method of claim 17, further comprising:
generating an R-wave sensed event signal in response to the ventricular electrical signal crossing the R-wave sensing threshold;
sensing an atrial electrical signal;
detecting atrial tachyarrhythmia from the atrial electrical signal;
temporarily disabling a post-atrial ventricular blanking period in response to detecting the atrial tachyarrhythmia;
determining that the R-wave sensed event signal is generated by the sensing circuit outside the post-atrial time interval when the post-atrial ventricular blanking period is temporarily disabled; and
disabling the post-atrial ventricular blanking period during the detected atrial tachyarrhythmia in response to at least the R-wave sensed event signal being generated outside the post-atrial time interval when the post-atrial ventricular blanking period is disabled.

29. The method of claim 17, comprising:
generating atrial pacing pulses;
sensing an atrial electrical signal;
generating a P-wave sensed event signal in response to the atrial electrical signal crossing a P-wave sensing threshold,
receiving the atrial event signal associated with one of an atrial pacing pulse or a P-wave sensed event signal;
setting the post-atrial time interval to a first time duration in response to receiving the atrial event signal associated with a P-wave sensed event signal; and setting the post-atrial time interval to a second time duration greater than the first time duration in response to receiving the atrial event signal associated with an atrial pacing pulse.

30. The method of claim 17, comprising:

adjusting the ventricular sensing control parameter by setting a safety pace interval in response to the atrial event signal;

generating an R-wave sensed event signal during the safety pace interval in response to the ventricular electrical signal crossing the R-wave sensing threshold during the safety pace interval;

generating a ventricular pacing pulse upon expiration of the safety pace interval in response to the R-wave sensed event signal being generated during the safety pace interval.

31. The method of claim 17, further comprising:

setting a post-atrial ventricular blanking period in response to the atrial event signal; and generating an R-wave sensed event signal in response to the ventricular electrical signal crossing the R-wave sensing threshold during the post-atrial time interval and outside the post-atrial ventricular blanking period.

32. The method of claim 17, comprising:

comparing the count of event time signals to first oversensing criteria when a post-atrial ventricular blanking period is enabled;

compare the count of event time signals to second oversensing criteria different than the first oversensing criteria when the post-atrial ventricular blanking period is disabled; and adjust the ventricular sensing control parameter in response to the count of event time signals meeting one of the first oversensing criteria or the second oversensing criteria.

33. A non-transitory, computer-readable storage medium comprising a set of instructions which, when executed by a control circuit of a medical device cause the medical device to:

sense a ventricular electrical signal;

set an R-wave sensing threshold;

receive an atrial event signal;

set a post-atrial time interval in response to receiving the atrial event signal;

generate an event time signal in response to the ventricular electrical signal being equal to or greater than the R-wave sensing threshold during the post-atrial time interval;

determine a count of event time signals in response to the generated event time signal; and adjust a ventricular sensing control parameter based on the count of event time signals.

* * * * *